(12) United States Patent
Pauli et al.

(10) Patent No.: US 8,236,564 B2
(45) Date of Patent: *Aug. 7, 2012

(54) AUTOMATED TITRATION METHOD FOR USE ON BLENDED ASPHALTS

(75) Inventors: Adam T. Pauli, Cheyenne, WY (US); Raymond E. Robertson, Laramie, WY (US); Jan F. Branthaver, Chatham, IL (US); John F. Schabron, Laramie, WY (US)

(73) Assignee: University of Wyoming Research Corporation, Laramie, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/816,278

(22) Filed: Jun. 15, 2010

(65) Prior Publication Data

US 2010/0251935 A1 Oct. 7, 2010

Related U.S. Application Data

(62) Division of application No. 10/467,181, filed as application No. PCT/US02/03983 on Feb. 5, 2002, now Pat. No. 7,736,900.

(60) Provisional application No. 60/266,555, filed on Feb. 5, 2001.

(51) Int. Cl.
*G01N 33/24* (2006.01)
(52) U.S. Cl. ............................ 436/29; 436/163; 436/164
(58) Field of Classification Search .................. None
See application file for complete search history.

(56) References Cited

U.S. PATENT DOCUMENTS

| | | | |
|---|---|---|---|
| 4,095,272 | A | 6/1978 | Janzen |
| 4,283,201 | A | 8/1981 | DeFord et al. |
| 4,628,204 | A | 12/1986 | Maes |
| 4,950,610 | A | 8/1990 | Tittle |
| 4,999,305 | A | 3/1991 | Wolcott et al. |
| 5,296,193 | A | 3/1994 | Reger et al. |
| 5,565,239 | A | 10/1996 | Pike |
| 5,924,794 | A | 7/1999 | O'Dougherty et al. |
| 5,990,206 | A | 11/1999 | Tanaka et al. |
| 6,048,447 | A | 4/2000 | Hayner et al. |
| 6,261,356 | B1 | 7/2001 | Isobe et al. |
| 6,773,921 | B1 | 8/2004 | Schabron et al. |

(Continued)

FOREIGN PATENT DOCUMENTS

WO 02/063292 A1 8/2002

OTHER PUBLICATIONS

Wiehe and Kennedy, "The Oil Compatibility Model and Crude Oil Incompatibility", Energy and Fuels, 2000, v. 14, pp. 56-59, published on Web Dec. 14, 1999.*

(Continued)

*Primary Examiner* — Yelena G Gakh
(74) *Attorney, Agent, or Firm* — Santangelo Law Offices, P.C.

(57) ABSTRACT

A system for determining parameters and compatibility of a substance such as an asphalt or other petroleum substance uses titration to highly accurately determine one or more flocculation occurrences and is especially applicable to the determination or use of Heithaus parameters and optimal mixing of various asphalt stocks. In a preferred embodiment, automated titration in an oxygen gas exclusive system and further using spectrophotometric analysis (2-8) of solution turbidity is presented. A reversible titration technique enabling in-situ titration measurement of various solution concentrations is also presented.

13 Claims, 12 Drawing Sheets

U.S. PATENT DOCUMENTS

2004/0058451 A1  3/2004  Pauli et al.

OTHER PUBLICATIONS

Carrier, H. et al., Acoustic Method for Measuring Asphaltene Flocculation in Crude Oils, Journal of Petroleum Science and Engineering, 27 (2000) pp. 111-117.

Parallel Indian Patent Application No. 998/kolm;/2003—E; Office Action dated Jul. 12, 2004.

Parallel Canadian Patent Application No. 2,437,652; Office Action dated Jul. 11, 2007.

Parallel Canadian Patent Application No. 2,437,652; Office Action dated Apr. 15, 2008.

Parallel Canadian Patent Application No. 2,437,652; Notice of Allowance dated Jul. 15, 2009.

Jones, G., et al. (1999), Development of an Ultrasonic Oil Stability Monitor for the Assessment of Asphaltene Aggregation in Hydrocarbon Streams, published in conference proceedings—Mitigation of Heat Exchanger Fouling and its Economic & Environmental Implications, Banff, Canada—United Engineering Foundation Conference.

"Annual Technical Report: Nov. 1, 1995-May 15, 1996"; Fundamental Properties of Asphalts and Modified Asphalts; Western Research Institute, pp. 303-331 (1996).

"Final Report—New Methods: vol. 2"; Fundamental Properties of Asphalts and Modified Asphalts; Western Research Institute; pp. 303-331 (1998).

Finnish Measurement Systems Ltd., "New Generation Porla—Laboratory Heavy Fuel Oil Stability Analyzer".

Finnish Measurement Systems Ltd., "Porla GLX" http://www.finnmeassys.com/Porla.htm; 4 pages, Aug. 1, 2003.

"Fundamental Properties of Asphalts and Modified Asphalts, vol. 1, Final Report, New Method"; Federal Highway Administration, 23 pp., Oct. 2001.

Heithaus, J.J., "Measurement and Significance of Asphaltene Peptization," Symposium on Fundamental Nature of Asphalt Presented Before the Division of Petroleum Chemistry, American Chemical Society, New York Meeting Sep. 11-16, 1960; 8 pp.

Heithaus, J.J., "Measurement and Significance of Asphaltene Peptization," Journal of the Institute of Petroleum, vol. 48, No. 458, pp. 45-53 (1997).

International Preliminary Examination Report for PCT/US02/03983, Feb. 5, 2002.

"Interpretive Final Report: Draft vol. 1"; Fundamental Properties of Asphalts and Modified Asphalts, Western Research Institute, pp. 303-331 (1997).

Pauli, A., "Asphalt Compatibility Testing Using the Automated Heithaus Titration Test," Western Research Institute, pp. 1276-1231 (1996).

Pauli, A., "Rheological and Compositional Definitions of Compatibility as they Relate to the Colloidal Model of Asphalt and Residual;" Symposium on Stability and Compatibility of Fuel Oils and Heavy Ends presented before the Division of Petroleum Chemistry, Inc., 217th National Meeting, American Chemical Society, Mar. 21-25, 1999; pp. 1990-193.

Pauli, A. and Branthaver, J., "Relationships Between Asphaltenes, Haithaus Competibility Parameters, and Asphalt Viscosity," Petroleum Science and Technology, 16 (9 & 10); pp. 1125-1147 (1998).

PCT application, WRI-Coke Index-PCT/US00/15950, filed Oct. 27, 2000, entitled "Predicting Proximity to Coke Formation."

PCT Application No. US/02/03983 entitled "Automated Flocculation Titrimeter System" filed Feb. 5, 2002.

"Quarterly Technical Report: Aug. 16-Nov. 15, 1999," Western Research Institute, pp. 177-197 (1999).

"Quarterly Technical Report: Nov. 16, 1999-Feb. 15, 2000," Western Research Institute, pp. 159-174 (2000).

"Quarterly Technical Report: May 16-Aug. 15, 1999," Western Research Institute, pp. 159-165 (1999).

Redelius, P.G., "Solubility Parameters and Bitumen," Fuel 79, pp. 27-35 (2000).

Reichert, et al., "Measurement of Asphaltene Flocculation in Bitumen Solutions," The Journal of Canadian Petroleum Technology, Sep.-Oct. 1986, Montreal, pp. 33-37.

"Standard Method for Automated Heithaus Titrimetry," ASTM Meeting, Aug. 2000, pp. 1-13.

Schabron, J. and Pauli, A., "Coking Indexes Using the Heithaus Titration and Asphaltene solubility," Symposium on Stability and Compatibility of Fuel Oils and Heavy Ends presented before the Division of Petroleum Chemistry, Inc., 217th National Meeting, American Chemical Society, Mar. 21-25, 1999; pp. 187-189.

U.S. Appl. No. 10/009,863 entitled "Predicting Proximity to Coke Formation," filed Dec. 12, 2001.

U.S. Appl. No. 60/138,846 entitled "Predicting Proximity to Coke Formation," filed Jun. 10, 1999.

U.S. Appl. No. 60/266,555 entitled "Automated Flocculation Titrimeter System," filed Feb. 5, 2001.

Zematra BV, "Automated Stability Analyser," for residual refinery streams and fuel oils; Feb. 24, 2001; 2 pgs.

Bartholdy et al., "Changes in Asphaltene Stability during Hydrotreating," Energy Fuels, 2000, 14 (1), pp. 52-55.

Peramanu et al., "Investigation on the Reversibility of Asphaltene Precipitation," Energy Fuels, 2001, 15 (4), pp. 910-917.

Schabron, J. F. et al., "Non-pyrolytic heat induced deposition from heavy oils," Fuel, 2001, v. 80, pp. 919-928.

U.S. Appl. No. 10/467,181, filed Aug. 4, 2003.

* cited by examiner

AUTOMATED TITRATION METHOD FOR USE ON BLENDED ASPHALTS

CROSS REFERENCES TO RELATED APPLICATIONS

This application is a divisional application of, and claims benefit of and priority to, U.S. patent application Ser. No. 10/467,181, filed Aug. 4, 2003 (published as publication number US 2004/0058451 A1 on Mar. 25, 2004) which itself is a US National Phase filing under 35 U.S.C. §371 of International Patent Application No. PCT/US02/03983, filed Feb. 5, 2002 (published as publication number WO 02063292 A1 on Aug. 15, 2002), said international application claiming benefit of and priority to U.S. Provisional Patent Application No. 60/266,555, filed Feb. 5, 2001, each of said patent applications hereby incorporated by reference.

ACKNOWLEDGMENT OF GOVERNMENT SUPPORT

This invention was made with federal government support under Cooperative Agreement No. US Department of Energy contract DE-FC26-98FT40322 awarded by the United States Department of Energy. The federal government may have certain rights in this invention.

TECHNICAL FIELD

This invention relates generally to titration methods and apparatus, and more specifically to automated titration methods and apparatus for accurate determination of Heithaus parameters and resultant accurate prediction of compatability of petroleum residua such as asphalt.

BACKGROUND

The Heithaus test, which models asphalt explicitly as a colloidal system, was developed in the early 1960's by J. J. Heithaus to study compatibility characteristics of petroleum residua used in the roofing industry. Since then, the Heithaus test has found use in the paving industry as a method to study rutting propensity and oxidative age hardening. The original method, which suffered from operator dependency and poor data repeatability, has recently been automated. An automated Heithaus titration (AHT) test has been developed based on light transmitting/scattering detection of the onset of flocculation using ultraviolet (UV)-visible spectrophotometry. The AHT test has been found to significantly reduce operator dependency and improve data repeatability, in some cases, by an order of magnitude. As a result of the improved repeatability of data, Heithaus parameters are found to measure physical properties that relate to rheological properties of asphalt.

Historically, asphalts have been classified into gel-type asphalts and sol-type asphalts. Gel-type asphalts usually are characterized by non-Newtonian rheological behavior, relatively low variation of viscosity with temperature, and low ductility. Sol-type asphalts exhibit more Newtonian rheological behavior, are highly temperature susceptible, and are more ductile. The two classifications represent extremes; most asphalts are of an intermediate nature. Sol-type asphalts have also been designated as compatible asphalts, while gel-type asphalts have been designated as incompatible asphalts.

The terms "compatible" and "incompatible" (or even sol and gel) arose from what became known as the colloidal model of asphalt structure and often are used as general terms to relate "self-compatibility" and "self-incompatibility". This model considers asphalts to be dispersions of what are termed "micelles," consisting of polar, aromatic molecules in viscous oils. In the model, the degree to which the so-called "micelles" form extended gel structures (which can be broken up by heat and shear) determines the relative degree of compatibility. In a compatible asphalt, the dispersed materials are believed to be well peptized by the solvent, either because the dispersed materials are small in amount and/or tend not to form strong associations, and/or because the solvent effectively disperses the "micelles." In an incompatible asphalt, associations of dispersed materials presumably are more extensive and are not so efficiently peptized by the solvent.

The colloidal model has been subjected to much criticism in recent years. The principal objection is that there is no evidence for "micellar" structures, either classical or inverse, in asphalts. The term "micelle," which implies the existence of a separate phase with distinct boundaries, may in fact be inappropriate. More recently, a different microstructural model of asphalt structure had been proposed. Even this has now been refined by the present inventors. In the model, associations of polar, aromatic molecules of varying sizes are considered to be dispersed in a solvent moiety composed of less polar, relatively small molecules. No distinct phase boundaries are believed to be present. Regardless of the validity of the model, though, the concept of compatibility as a measure of mutual miscibility of different chemical components of asphalts is still useful. Compatible asphalts differ from incompatible asphalts in their physical properties and therefore may be expected to behave differently in pavements. Changes in the degree of compatibility often have opposing effects on important performance related properties. For example, a change that may result in better rutting resistance may also result in more embrittlement resulting from oxidative age hardening. Thus, compromises in compatibility can be viewed as necessary for optimum overall pavement performance.

Asphaltenes are solid materials that precipitate when asphalts are treated with solvents such as n-pentane, n-hexane, n-heptane, iso-octane, etc. Maltenes are the components of asphalts not precipitated by the above alkane solvents. Asphaltenes are more aromatic than maltenes and contain more heteroatoms. Thus intermolecular interactions are likely more extensive in asphaltenes than in maltenes. This may be reflected in the greater molecular weights of asphaltenes compared with maltenes. In the colloidal model of asphalt structure, asphaltenes are believed to correspond to the dispersed materials and maltenes to the solvent. Therefore, asphaltenes may be mainly responsible for the internal structure of asphalts and may dominate many physical properties. Thus the amount of asphaltenes in an asphalt could be one measure of compatibility. Compatible asphalts may have smaller amounts of asphaltenes than incompatible asphalts. The ease with which asphaltenes are dispersed may be dependent on their peptizability and on the dispersing power of maltenes. Oxidative aging of an asphalt could be predicted to influence compatibility by formation of polar molecules, which may result in more extensive molecular associations, but also may result in a better solvent.

The best known measurement of compatibility of asphalts that takes all the above factors into account is the Heithaus test. Heithaus observed that for straight-run asphalts, measuring asphaltene contents provided a reasonably good estimate of compatibility. Perhaps surprisingly, in blended asphalts from different sources (composite asphalts or asphaltic composites), weight-averaging asphaltene contents did not provide reliable estimates of compatibility. It thus was viewed as necessary to test each blend and develop a different method that took into consideration factors other than asphaltene content. In Heithaus' original "classical" test, solutions of various concentrations containing different weights of asphalt ($W_a$) were dissolved in a constant volume of solvent ($V_S$), e.g., toluene or benzene, were titrated with normal alkane solvents, including, e.g., n-heptane, until flocculation (asphaltene precipitation) was observed. Flocculation was detected by spotting a drop of the solution onto filter paper, to permit the resulting phase separation of precipitated material from material remaining in solution to be observed. This was done by a direct observation or through the use of a microscope. The volume of titrant ($V_T$) required to initiate flocculation in each solution was then used to determine flocculation ratios (FR), calculated as $FR=V_S/(V_S+V_T)$. Values of flocculation ratios were plotted versus dilution concentration (C), calculated as $C=W_a/(V_S+V_T)$ and a best fit straight line connecting the points was extrapolated to the x- and y-axes. The x and y intercepts determined from the extrapolation, referred to as the dilution concentration minimum ($C_{min}$) and the flocculation ratio maximum ($FR_{max}$), respectively, were used to calculate three Heithaus parameters, defined below.

The theoretical significance of the quantity $C_{min}$ was that it represented the quantity of titrant (n-heptane for the classical method) that would be just enough to cause asphaltene precipitation in the neat asphalt, undissolved in toluene, assuming it would be possible to do so. $FR_{max}$ represented a measure of the solubility parameter, δ, which may be measured in Hildebrand units, H, at which asphaltene flocculation occurred in the asphalt as a whole. Thus, the Heithaus method measured some fundamental properties of asphalts and blends that asphaltene concentration values did not measure.

In the original "classical" test, the Heithaus parameters were: $p_a=1-FR_{max}$, which measured the peptizability of the asphaltene fraction; $p_o=FR_{max}(C_{min}^{-1}+1)$, which measured the solvent power of the maltene fraction, and $P=p_o/(1-p_a)$, which measured the overall compatibility of the asphalt. Larger values of $p_a$, $p_o$, and P represented peptizable asphaltenes, maltenes that were a good solvent, and a compatible asphalt overall. Smaller values of $p_a$, $p_o$, and P represented the reverse. Interestingly, the $p_a$ and $p_o$ values did not necessarily vary directly with one another among asphalts. An asphalt may be composed of asphaltenes that are not readily peptizable, but which are dispersed in maltenes that have good solvent characteristics, or the reverse.

DISCLOSURE OF INVENTION

As alluded to earlier, the original "classical" test can be tedious and can yield highly variable results, especially with waxy asphalts. Thus, an improved compatibility test has be long desired. As the present inventors recognized, a study of asphaltene flocculation behavior was needed to develop an improved compatibility test. As a result, initially a basic automated Heithaus titration procedure was developed based on methods for determining asphaltene precipitation characteristics. That basic procedure has now been refined to make it practical and commercially valuable.

MODE(S) FOR CARRYING OUT THE INVENTION

Figure 1:
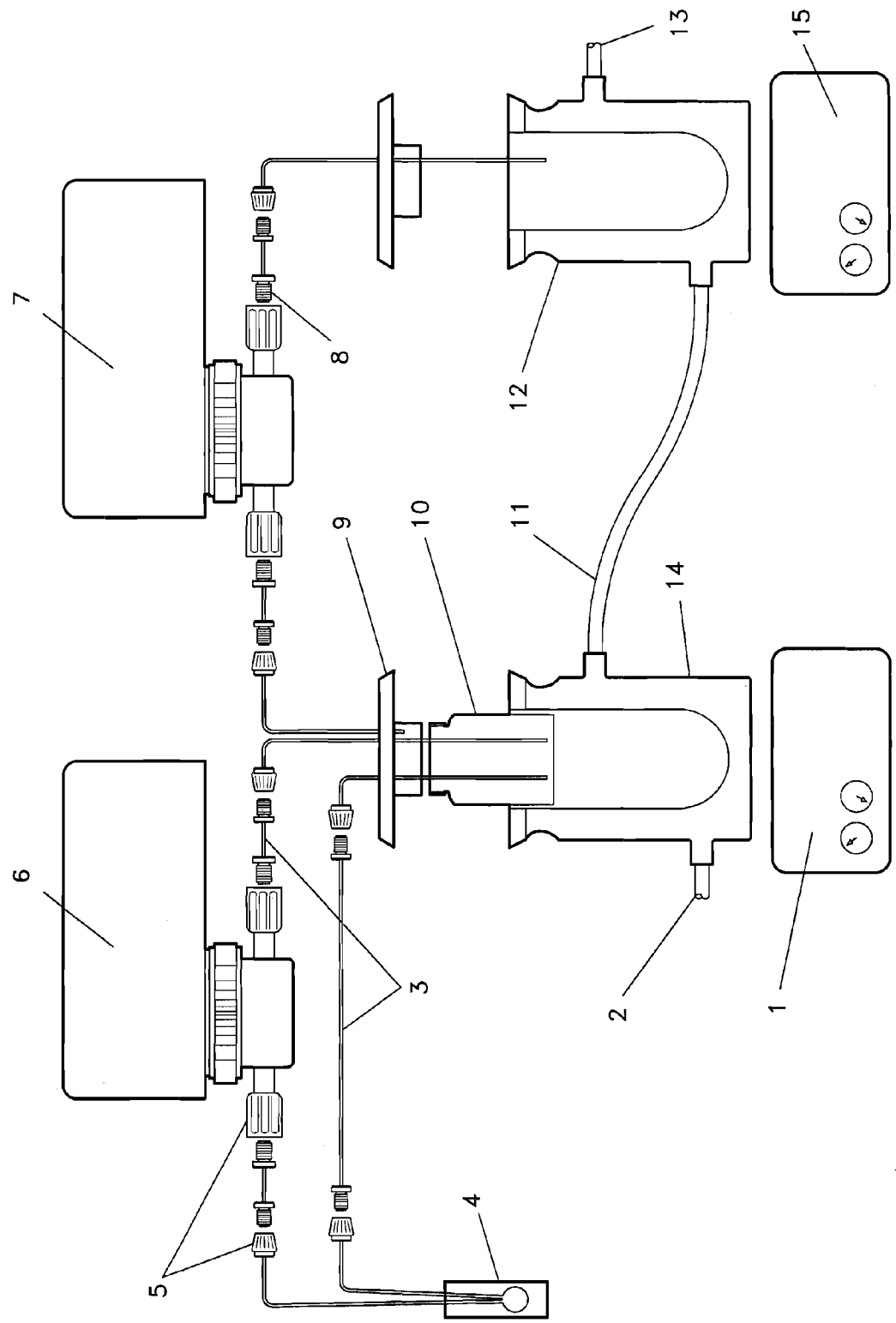
FIG. 1. The titration portion of one embodiment of the automated test apparatus is shown schematically in FIG. 1 with:
1. Stir Plate
2. Inflow from Circulating Water Bath
3. 1/16" I.D. Tubing
4. 0.1 mm Pathlength Quartz Flow Cell (To Be Housed in Spectrophotometer)
5. Tube End Fitting Adaptors
6. Circulation Pump (High Flow Rate Metering Pump)
7. Titrant Pump (Low Flow Rate Metering Pump)
8. Fitting for 1/16" I.D. Tubing
9. Teflon Cover
10. 30-mL Vial
11. Neoprene Tubing
12. Water-Jacketed Titrant Vessel
13. Outflow to Circulating Water Bath
14. Water-Jacketed Reaction Vessel
15. Stir Plate FIG. 2. An alternative design for the titration portion of the automated test apparatus is also shown schematically in FIG. 2 with:
16. FMI Metering Pump
17. FMI Dispersing Pump
18. Sample Vial with Water Jacket
19. Flow Cell with Teflon Cover
20. Cell Holder
21. Light Source
21a. Fiber Optics Cable
22. PC (type) Computer
23. UVvisable Spectrophotometer
24. Titrant Reservoir
25. Stirring Plate FIG. 3 A possible design with dimensions of one embodiment of the solution containment element is shown in FIG. 3 with:
A Top View
B Profile View FIG. 4 A possible design with dimensions for one embodiment of the solution containment element is shown in FIG. 4 with:
A Top View
B Profile View FIG. 5

Accordingly, the present invention provides improved and automated methods to determine various properties of substances such as asphalts in a manner which is practical and commercially valuable. As may be understood, the invention discloses methods and apparatus which may be combined and utilized in a variety of manners. Importantly, while some methods and devices are disclosed, it should be understood that all of these can be varied in a number of ways. Importantly, as to all of the foregoing, all of these facets should be understood to be encompassed by this disclosure.

In one embodiment, the test method may be used to measure the compatibility or colloidal stability of asphalt and heavy residua, such as petroleum residua, by determining the flocculation onset, i.e. the point at which asphaltenes just begin to precipitate from a solution of known weight sample prepared in a "solvent" and titrated with a "non-solvent", resulting in a change in a solution turbidity, which may be indicated by a change in transmittance as may be measured by a spectrophotometer, also referred to as a spectrometer. The advantages of the automated method are that it can act to monitor asphalt flocculation by observing sharp or more gradual changes in transmittance—such as at 740 nm or the like—of the solution being titrated. Such methods can be designed so as to not be as operator dependent as the original method. Importantly, the improved automated Heithaus method may now be used for the testing of not only neat asphalts, but also asphalt blends (e.g., blends of asphalts from one or more different stocks), and even oxidatively aged asphalts.

In order to understand the improvements now disclosed, it may be helpful to understand that the Heithaus asphaltene peptizability parameter, $p_a$, is to some degree now viewed as related to asphalt rheological properties in terms of the Pal-Rhodes equation. The $p_a$ values may be used to directly measure the volume fraction (a) of the continuous (maltene "solvent") phase immobilized by the flocs of solvated asphaltene particles in an asphalt. Thus, reasonable Pal-Rhodes solvation parameters ($K_S$) values (which measure the size of the solvation shell, and may be related to the stability of the asphalt system), may now be determined based on $p_a$ data. This aspect in part facilitated the development of the improved automated procedure now disclosed.

In order to comprehend the improved automated procedure it may also be helpful to understand the overall system. Systems according to the present invention can, of course, take many forms. Of the many variations possible, the following list of scientific equipment or supplies may be utilized in one illustrative design:

Hach DR/3000 UV-visible spectrophotometer or a 2 channel OceanOptics PC2000-UV-Vis General Purpose Spectrometer (Hach Co. and Ocean Optics, Inc.), which may include the following items:
one or more 1 MHz PCI-bus A/D card w/grating or 1 MHz ISA-bus A/D cards w/#3 Grating (350-1000 nm) (master and slave channels)
one or more cuvette holders—VIS, 1 cm Path
one or more 100µ patch optical fibers
one or more (in-line fiber optic) attenuators such as FVA-UV Fiber Optic Variable Attenuators
a 3100K, 12V tungsten Halogen light source
a 200µ bifurcater optical fiber
one or more 25µ slit gratings (#3-installed on A/D cards)
a SMA splice bushing assembly
Spectra-Physics SP4270 integrator (Spectra-Physics Inc.)
ChronTrol®, Model XT-4 power switch timer (ChronTrol Corp.)
two CGS® 200 mL reaction vessels (water jacketed)(CGS/Thermodynamics)
two FMI® metering pumps, Models: QG-50 w/R405 pump head (circulation pump; P1) & QG-20 w/RH00 pump head and RH/Q fit kits (titrant dispersion pump; P2) (Fluid Metering, Inc.)
one or more RHSYOOSTYLF PIP Pump w/fit kits (Fluid Metering, Inc.)
NesLab RTE-110 or 111M Temperature controlled circulating water bath (Neslab Instruments, Inc.)
a Remote Sensor
Starna® 0.1 mm or 0.5 mm flow cells (such as from Starna Cells, Inc.) w/Teflon® tubing and fittings
30 mL vials adaptable to Teflon® flow cell cover (VWR Scientific Products Corp.)
0.056 cm ID (0.022") and 0.159 cm ID (1/16") Viton® tubing (VWR Scientific Products Corp.)
one or more Kontes 200 mL water jacketed reaction beakers
one or more Teflon® reaction caps/reactor covers (adaptable to 25-40 mL reaction vials)
one or more VWR Model 200 Magnetic Stirrers
one or more 0.5 mm Quartz flow cells w/Teflon® tubing and fittings
one or more lab jacks
one or more 25-40 mL test tube reaction vials (cap threaded, w/Teflon® seals)
7/16" OD×5/16" ID Vinyl tubing (for water flow)
one or more Teflon® elbows
one or more 1/4"×28 to Luer Lock fittings one or more flange fittings
one or more Flange Ferrule fitting kits
Teflon® tubing (1/32" ID)
one or more Magnetic stirring plates
Reagents such as the following may also be used:
  Toluene of reagent, LC or HPLC grade (VWR Scientific Products Corp.)
  Iso-octane (2,2,4-trimethylmethane) LC or HPLC grade (EM Sciences) HPLC grade 2-Butanone (methyl ethyl ketone)
  HPLC grade 2-ethyl-1-hexanol (iso-octanol).
Further, the following analysis and computer equipment may be used:
  IBM-compatible PC (500 MHz minimum processing speed recommended)
  384(+)ST-RAM Memory
  10 Ge(+)Hard Drive
  MS Windows 98 w/Excel 5.0
  100 MHz ZipDrive
  8-MHz HP Laser Printer
  NesCom Software package
  RS232 "null" 9-pin cable w/male-female adaptors.

Generally, a representative method may be accomplished as follows. Solutions of heavy residua or asphalt may be dissolved in toluene or other higher solubility solvents (e.g., the group consisting of toluene ($\delta$=8.9H; where H is Hildebrand units) and benzene), may be prepared in small volume reaction vials (e.g., 25 mL) and may titrated with solvents of lower solubility (e.g., the group consisting of aliphatic hydrocarbon substances (such as iso-octane, $\delta$=6.9H) and alcohol substances). The added solvent amount (and the soluble substance amount) may be noted. The term solution is used herein in a general sense and may even include what are more specifically referred to as colloids. Any petroleum residua that is mixed with a solvent is referred to as a solution, as is the mixture resulting from the addition of titrant to a petroleum residua/solvent mixture. The term dissolve is similarly defined broadly, to include even mixing that results in a colloid. Titrations may be performed by following a titration method and by using a titration apparatus, generally by first creating a solution by dissolving a soluble substance such as petroleum residua such as asphalt into or by using a solvent (more generally mixing a petroleum residua with a solvent), and then delivering a titrant (e.g., by controllably adding at titrant, and/or continually adding a titrant) at a constant flow rate via a metering pump to this test solution via a pipe from what is termed generally as a titrant containment element. Any type of titrant delivery element may be used to deliver titrant to a container of solution, more generally referred to as a solution containment element.

Test solutions, which may be prepared at several initial concentrations $W_a/V_S$ ($W_a$: weight of asphalt and $V_S$: initial volume of solvent) in 25 mL "test tube" reaction vials, may be temperature controlled by housing the reaction vials in water jacketed beakers temperature regulated with a circulating water bath. More generally, test solution(s) may be temperature controlled by a temperature maintenance element, which may maintain the solution at a desired temperature. The temperature maintenance element may comprise a solution containment element heat transfer element (which may comprise a jacketed beaker that surrounds the solution beaker and contains a circulating heat transfer fluid) and a titrant containment element heat transfer element (which similarly may comprise a jacketed beaker that surrounds the titrant beaker and contains a circulating heat transfer fluid). The two heat transfer elements may be joined via tubing, or fluidically connected, so as to form a joined heat transfer system. Two elements are fluidically connected if fluid from one may flow to the other. The temperature maintenance element may include a fluid pump.

The end point of the titration, referred to as the flocculation onset point, can be measured from percent light transmission versus time experiments using a spectrometer, in the capacity of a flocculation onset detection element such as a turbidity detector. More generally, a solution threshold change detector, or more generally, a solution change detection element, may be used to detect any change in the solution such as solubility reduction response such as flocculation. Detection may be accomplished automatically by a solution change index monitor such as a solution turbidity monitor (also more specifically referred to as a flocculation onset monitor) such as a spectrophotometer, which may also be referred to more generally as, among other terms, an automatic solution character determination element. This detection may be achieved by monitoring a solution change index such as turbidity. Spectrophotometrically analyzing the solution may be accomplished by circulating the test solution with a second metering pump, through a short pathlength flow cell, or more generally a flow cell element. A solution circulation system may deliver solution from the solution containment element to the flow cell and back to the solution containment element, perhaps using a solution pump. A solution change detection element may be responsive to said flow cell element. A first discrete element, such as, for example, a structural member, is responsive to a second discrete element if the first discrete element reacts or responds in some way to the second discrete element. As with the spectrophotometer, it may be configured to detect a change in light transmittance. Time data corresponding to $V_T$, the minimum volume of titrant required to initiate flocculation onset may be determined based on t at maximum % T. Heithaus compatibility parameters $p_a$, $p_o$, and P, which can relate to colloidal stability, may be calculated from initial condition and flocculation onset data ($W_a$, $V_s$, and $V_T$).

Upon achieving a threshold solution change such as flocculation, a parameter such as an added titrant amount and/or a time since the initiation of titrant addition until threshold change may be determined or assessed. Upon such assessment, determining a characteristic (e.g., determining at least one Heithaus parameter, or a compatibility measurement) of at least one substance of said solution may then be the next step in the titration method.

It is important to note that the entire titration method and system may be electronically automated. Such automation may include automatically activating electronic components. It may also include electronic (including computerized) monitoring of parameter values such as turbidity and maximum % light transmittance, in addition to automatic activation of certain functions or components upon determination of a certain event (e.g., automatic delivery of additional solvent upon the determination of maximum % light transmittance in the reversible titration procedure). It may comprise automatic determination of a Heithaus parameter(s), as well as automatic determination of, for example, added solvent amounts and/or added titrant amounts, as well as of time of metered addition of titrant.

Figure 2:
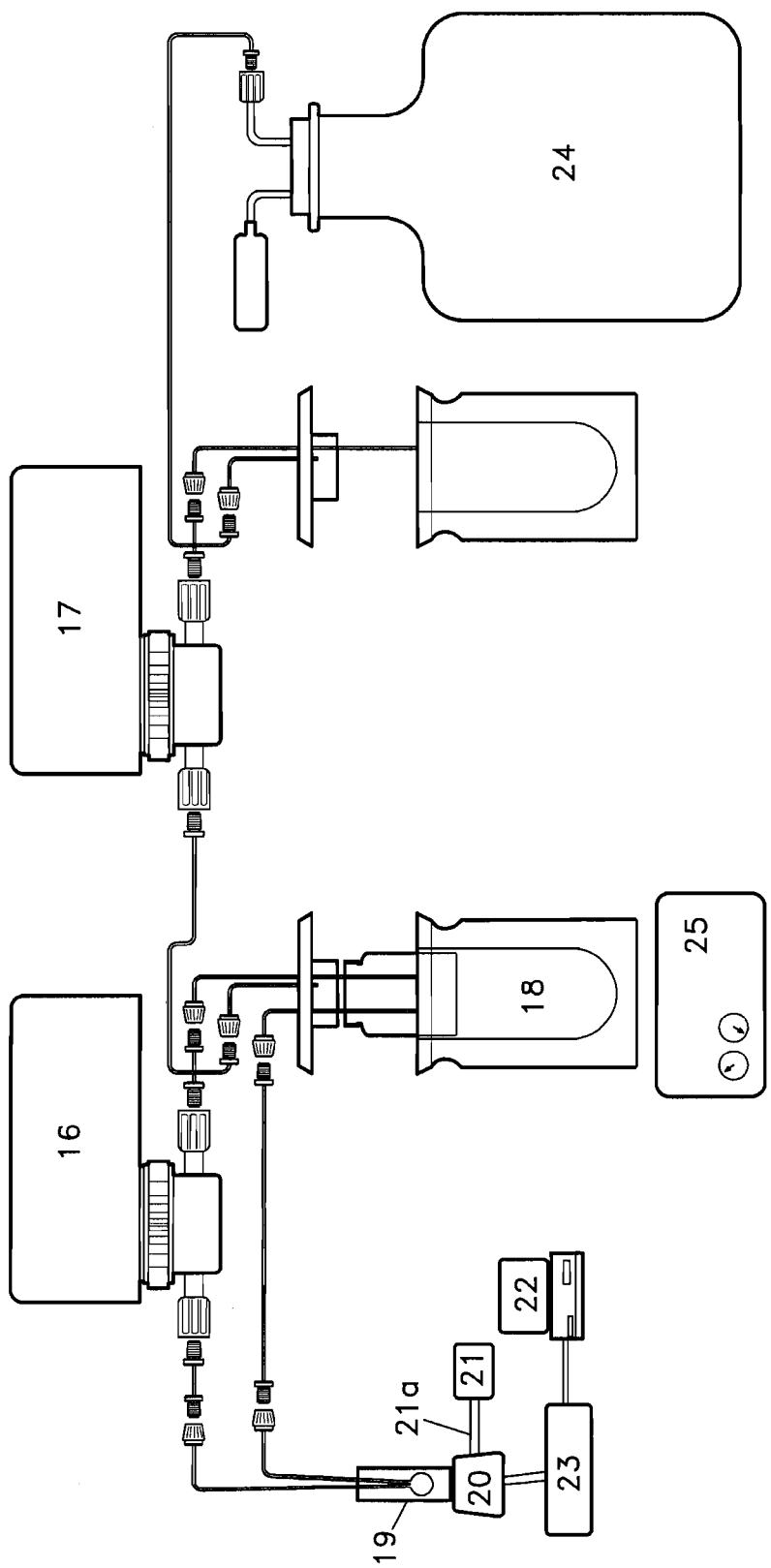
Figure 10:
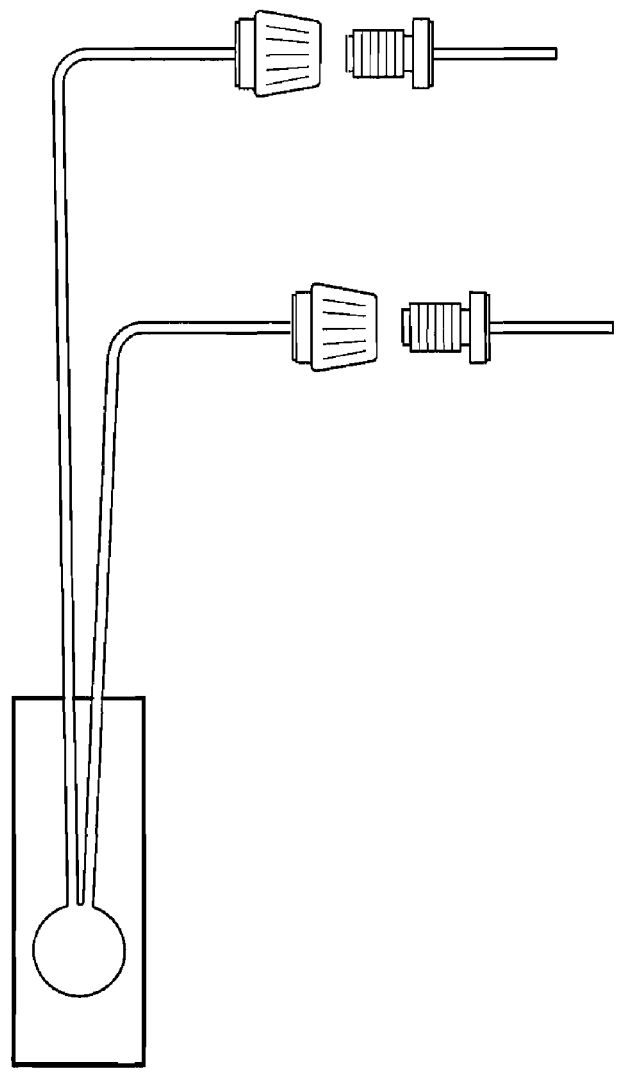

In more detail, and using the above materials, a prototype system may be assembled as follows. A schematic of one embodiment of a prototype overall system is shown in FIG. 1. The various components of this and other illustrative systems are shown in more detail in other figures. For example, FIG. 2 shows another embodiment of the titration portion of the prototype design. Schematics of embodiments of 30 mL vials (33) with a Teflon® flow cell cover (19) is shown in detail in FIGS. 3 and 4. The stir plates (1), (15), an 25, lab jacks, water jacketed reaction beakers (14), and cuvette holders may be configured as shown in other figures. A flow cell (19) embodiment is shown in FIG. 10.

As may be appreciated, the water jacketed reaction beakers and cuvette holders may be plumbed to a refrigerated bath/circulator using 7/16" OD×5/16" ID Vinyl tubing (31), (32, and (44), assorted Teflon® or vinyl 45° elbows (5/16" OD) and couplers (5/16" OD). The tubing, couplers, and elbows may be fastened using plastic hose clamps or the like, of course. Further, as shown, the vinyl tubing and water jacketed reaction beakers may be insulated with styrofoam refrigeration tubing and black duct tape or the like. The refrigerated bath/circulator RS232 port may be connected to the computer cable serial port using a 6'-RS232 "null" 9-pin cable.

Cuvette holders and metering pumps may also be configured to the lab jacks as shown. A sample circulator and one or more circulator metering pumps may be plumbed to the flow cells and sample reaction vials using Teflon® tubing and fittings (8), which are internally coated with a Teflon® surface coating, as may be any other pipings, conduits, caps, or containers. More generally, such system components may have a reduced flow resistance internal surface. Other coatings other than Teflon® that similarly reduce frictional force exerted against a passing fluid may be used also, or no special coating over the internal surface of the tubing may be used at all. A titrant dispenser may also be used. In some embodiments, a stand or platform may be utilized directly behind or adjacent stir plates (1), (15), an 25 and lab jacks. As shown, it may be desirable to place each titrant pump (7) on a stand, directed toward the reaction beaker to which it will titrate. Further, the titrant pumps may be plumbed to the titrant reservoir (24) and (41) and sample reaction vials w/Teflon® reaction caps (or lids)/reactor covers using a 2-RH/Q Fit Kit (Teflon® tubing (e.g., 1/32" ID) and Flange fittings. A Luer-Lock coupler may be fastened to the tubing end leading to the reaction vial from the titrant pump (7). A short-needle syringe (e.g., blunt ended-19 gauge, 1" long needle) may be inserted into Luer-Lock couplers. 50 mL beakers or the like may be placed adjacent to the pumps to hold-in-place the syringe needle-tubing ends.

As mentioned, FIGS. 1 and 2 show schematics of prototype apparatus used to perform automated titration tests. Power supplies running from the spectrophotometer, integrator (53), and water bath, circuits A (50), B (51), and C (52) respectively, may be connected to a ChronTrol® power switch timer (49), or more generally a system activation element. This can permit programmable activation of the instruments. Additionally, or instead, a computer such as a personal computer for example, may be configured to electronically interact with one or more of the following—a spectrophotometer, an integrator, any pumps that may exist, and a ChronTrol® power switch (49). A computer may be used in place of either the ChronTrol® power switch (49) and/or the integrator (53). Any device that may indicate the onset of a solution change, including but not limited to an integrator, a personal computer, or a combination of the two, may generally be referred to as a threshold change indicator, or more specifically, a light transmittance threshold change indicator.

Two CGS® 200 mL reaction vessels (water jacketed) (14) arranged in series may be attached to the water inlet (2) and outlet (13) of the NesLab RTE-110 circulating water bath. An FMI® metering pump (16), (38), and (43), Model QG-50 w/R405 pump head (P1) may be connected to the Starna® 0.1 mm pathlength flow cell (housed inside of the spectrophotometer) via a 15 cm long, 0.159 cm (1/16") ID piece of Viton® tubing (3). A second and third piece of 0.159 cm (1/16") ID Viton® tubing (3), 10 cm and 20 cm long, respectively, may extend from the metering pump and from the flow cell (19) to a 30 mL reaction vial screwed (33) into a Teflon® cover (27). The reaction vial w/Teflon® cover (33) may be positioned inside of one of the CGS® 200 mL water jacketed reaction vessels (WJ2) (34) and (46). A second FMI® metering pump (P2) (43), Model QG-20 w/RH00 pump head (titrant dispersion pump) may be connected to the other CGS® 200 mL water jacketed reaction vessel (14), which may act as a titrant reservoir (TR) (41), via a 25 cm long piece of 0.056 cm (0.022") ID Viton® tubing (32). A second, 20 cm long piece of 0.056 cm (0.022") ID Viton® tubing (32) may extend from the titrant pump (P2) (7), through a predrilled hole in the Teflon® cover (27) to the reaction vial positioned inside of a CGS® 200 mL water jacketed reaction vessel (WJ2) (34), and (46).

The spectrophotometer, temperature bath, and integrator (53) may be activated (circuits A, B and C) (50, 51 and 52 respectively) at least about 1 hour before testing of samples begin. As one way to achieve activation and automation, all three devices may be connected to a ChronTrol® power switch timer and may be activated by typing "CIRCUIT", "1", and "ON", "CIRCUIT", "2", and "ON", and "CIRCUIT", "3", and "ON" on the ChronTrol® power switch timer key pad. The temperature bath may be set to a temperature of 25° C. (77° F.). Fine tuning of the temperature control or feedback may be required once the temperature of the water bath has stabilized (e.g., in approximately 1 hour).

Liquid Chromatography-, LC-grade iso-octane (titrating solvent) may be added to the titrant reservoir (TR) (41). The level of titrating solvent may be added to within 1 cm of the top of the reservoir. Titrant may be added to the reservoir prior to activation of the water bath, allowing the titrant to also come to temperature equilibrium.

The spectrophotometer and integrator parameters may be set once the spectrophotometer has warmed up. The UV-visible spectrophotometer (23) and (36) can be set in percent transmittance detection mode by depressing "4", "signal", and the "% T" keys on the spectrophotometer soft key pad. The wavelength selection knob may be set to 4 (nm)=740 nm The zero scale and full scale settings of the spectrophotometer may be initially set at 0 percent transition and 100 percent transition, respectively, by depressing the following keys on the soft key pad of the spectrophotometer: "zero", "0", and "full", "1", "0", "0". Further, it should be noted that it may be desirable or necessary to reset the full scale and zero scale settings for each sample, depending on the sample response once testing has begun.

The spectrophotometer signal average is set to 10 by keying in: "signal", "1", "0". The integrator, when activated, may then prompt the user for the date and time. Once the date and time are entered the following settings may be entered on the soft key pad: "shift", "shift", "P", "W", "=", "shift", "2", "0", "0", "enter". This may represent one way of setting the peak width to 200. Further the commands: "shift", "shift", "P", "T", "=", "shift", "1", "0", "0", "enter", may be entered to set the peak threshold to 100. Attenuation may be set to 1024 by the commands: "atten", "1", "0", "2", "4", "enter". The chart speed may then be set to 1.0 cm/min using the commands: "chtsp", "1", "enter".

The following procedure may be used to re-zero the spectrophotometer relative to a toluene reference blank prior to sample testing. Two 30 mL vials may be joined or taped together and toluene may be added to one of the vials. The two joined-together vials may be placed in a ring stand clamp next to the solution circulating pump (P1) (38). Toluene may then be drawn from the first vial and deposited into the second (empty) vial, via Viton® tubing attached to the circulating pump (P1). When approximately one half of the toluene has been pumped into the second (empty) vial, the "re-zero" key on the spectrophotometer key pad may be depressed. The reading on the spectrometer may then read 100.0 percent transmittance. This may fluctuate perhaps ±0.5 percent transmittance. During the re-zeroing of the spectrophotometer, the solution circulating pump (P1) may be adjusted to a flow rate of 8 mL/min. The end of the Viton® tubing in the vial containing toluene may be removed and the circulating pump system may be pumped clear of solvent.

Figure 3:
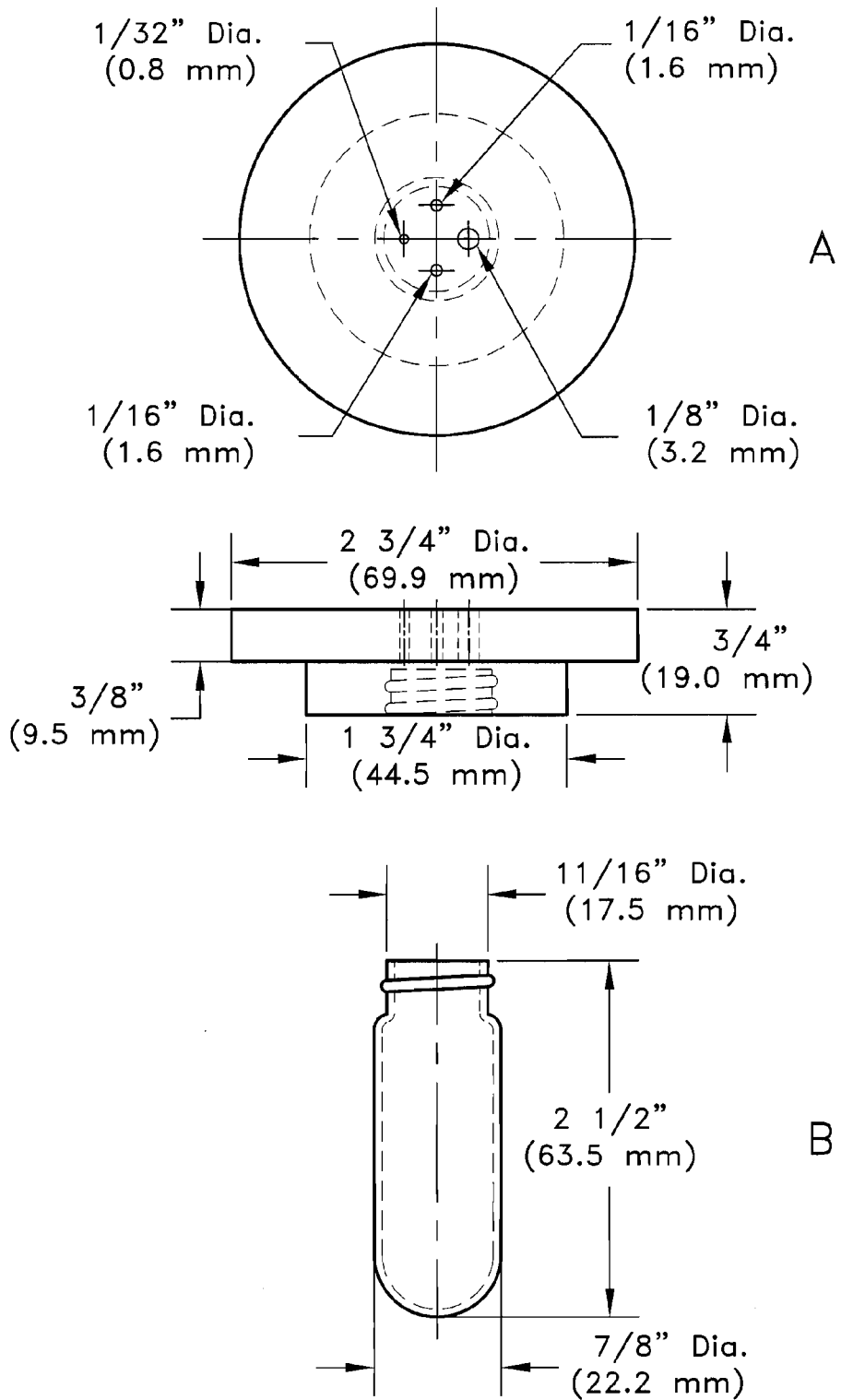
Figure 4:
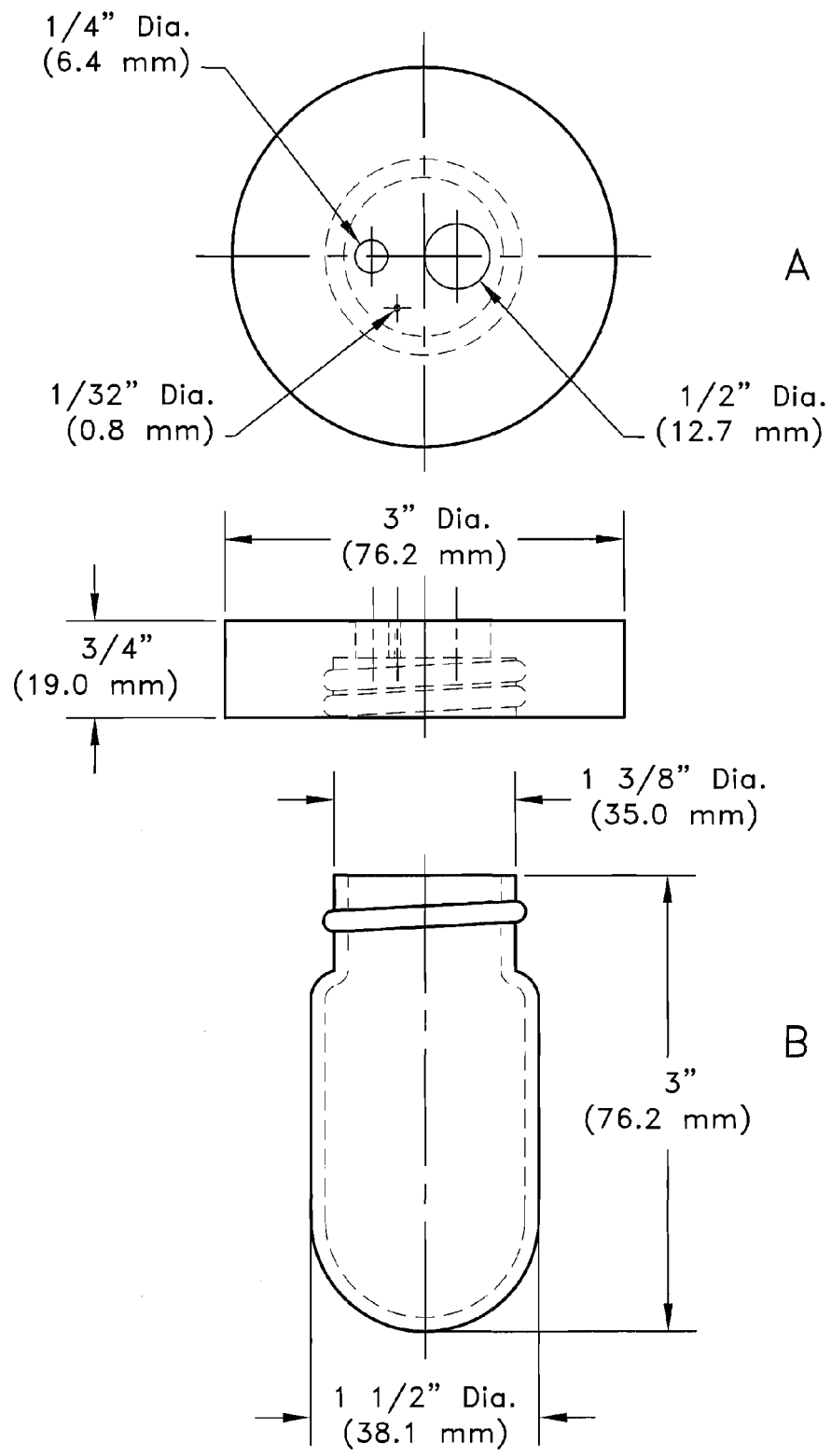

The samples may then be prepared as follows. Samples of asphalt may be weighed into 30 mL vials adaptable to a custom design Teflon® cover (27) as shown in FIGS. 3 and 4. Care may also be taken during weighing not to deposit asphalt on the sides of the vials. Two sets of the following representative sample weights may be prepared; 0.200 g, 0.400 g, 0.600 g, and 0.800 g (all ±0.002 g). The actual measured weight of each sample, measured to an accuracy of ±0.0002 g, may then be recorded as $W_a$. Samples may then be labeled with information such as: Operator initials; notebook number; page number; sample set letter; sample number. Of course, several sets of samples may be weighed into vials at one time. Here, it may be noted that if dry samples are to be stored for any length of time, e.g., more than a day or perhaps more than even just 4 hours, it may be desirable for them to be capped under a blanket of argon gas.

The samples to be tested within 1 day of weighing may then be dissolved in 1.000±0.002 mL of LC-grade toluene. This may be added to each vial using a 2.500±0.002 cc syringe. The volume of solvent added to each sample may then be recorded as $V_S$. Approximately 1 to 2 hours may be required to completely dissolve all samples at room temperature. For best results it may be desirable for samples dissolved in solvent to be tested on the same day they are prepared.

Figure 9:
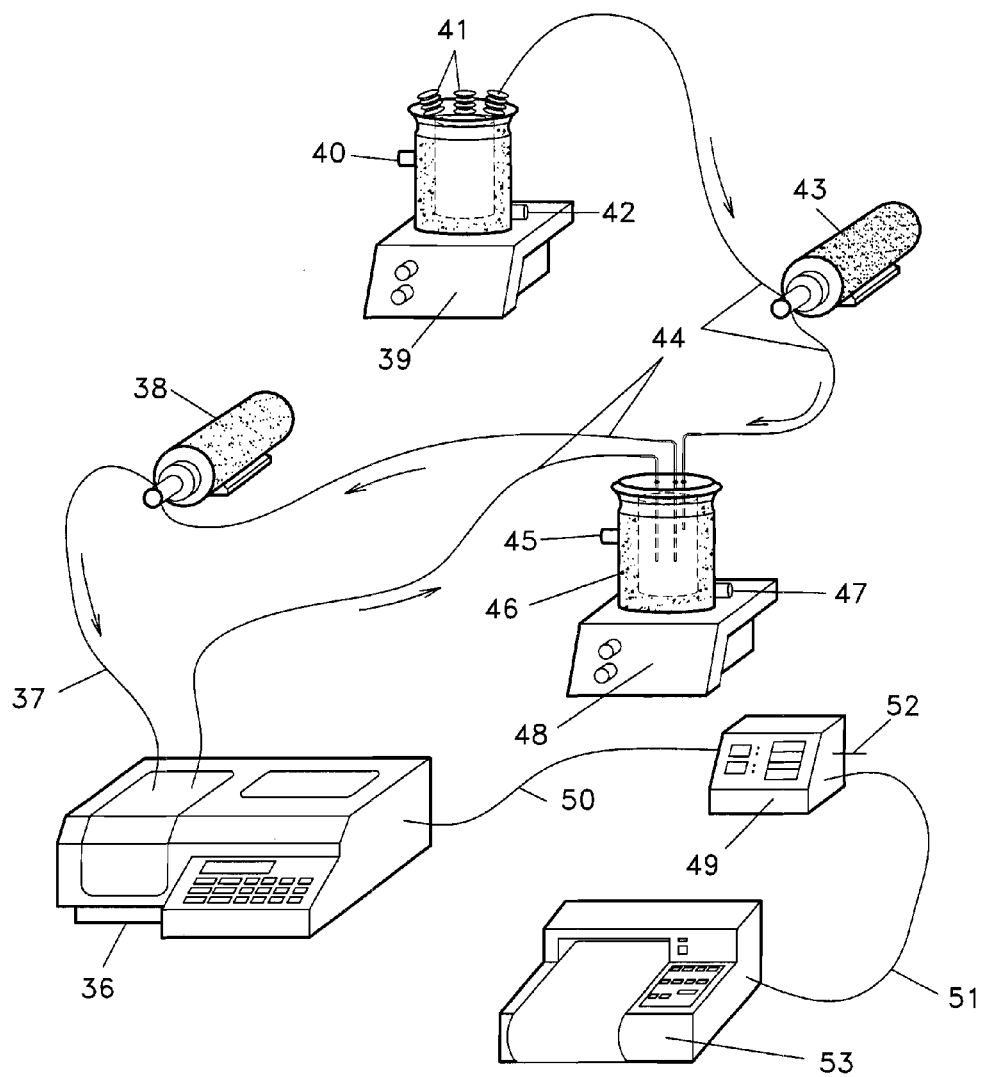

As an improved design, a solution circulation system (SCS) may be assembled as shown in FIGS. 1, 2, and 9 as follows. The SCS may be assembled using a RHSYOOSTYLF PIP" FMI fluid metering pump, 1/32" ID-Teflon® tubing and Flange Ferrule fitting, and a 0.1-0.5 mm flow cell. The leg stands originally provided with the pump may be modified by installing 2½" leg extensions to each of the four legs of the pump. This may allow the pump to sit high enough, directly over the flow cell cuvette holder, and adjacent to the Kontes 200 mL water jacketed reaction beaker to operate properly. The pump may be specified to have a ⅛" piston diameter with a maximum piston travel distance of ¼". This may help to reduce the volume of test solution in the SCS at any given time period during the analysis. Three pieces of 1/32" ID-Teflon® tubing may be fastened between the pump and flow cell, flow cell and reaction vial, and from the pump to the reaction vial using Flange Ferrule fittings. The lengths of Teflon® Tubing used may be 7-8 mm, 4-5 mm, and 15-16 mm, respectively. The total volume of the SCS might be designed so as not to exceed ~10% of the volume of the starting test solution. The circulation rate of the SCS may also be maintained at a minimum flow rate of 8.0 mL/min, where faster flow rates are permitted. The "RHSYOOSTYLF PIP" FMI fluid metering pump may be further specified to have an organic solvent resistant piston sleeve.

As mentioned, it may be desirable to design the total volume of the SCS so as not to exceed ~10% of the volume of the starting test solution, or in other words, 10% of an initial solution volume, where initial refers to the time before any addition of titrant. The SCS may thus be a low volume solution circulation system. This may serve to reduce or eliminate "Flocculation Peak Shift". Flocculation Peak Shift may be characterized by flocculation peaks being shifted to lower values of flocculation onset. This may be due to too large of a volume of test solution (e.g., >about %10) residing within the SCS, relative to the volume of solution in the vial during a test run. With the current configuration, test solutions are prepared using 0.8 g, 1.0 g, 1.2 g, etc. of test sample (asphalt) per 2.0 mL of solvent (toluene). This may serve to eliminate any significant flocculation peak shift.

Figure 8:
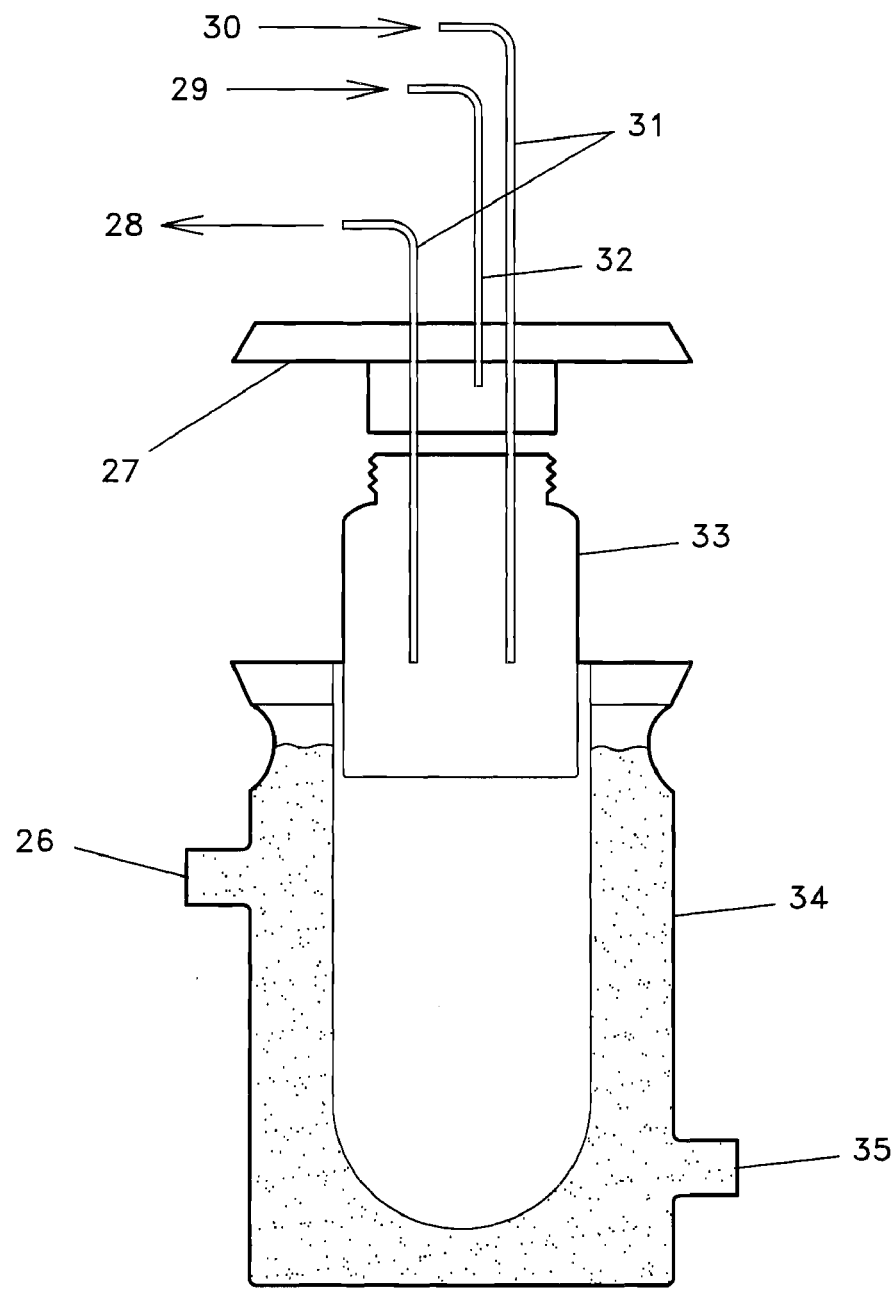
FIG. 8 One possible embodiment of AHT w/iso-octane reaction vessel consisting of a 100 mL (optional or 200 mL water jacket, 30 mL sample vial, and a custom designed Teflon cover/vial holder with:
26. $H_2O$
27. Teflon Cover
28. Out to Flow [Ceil] Cell
29. In from Titrant
30. In from Flow Cell 31. 1/16" ID Viton or Teflon Tubing
32. 0.022" ID Viton or Teflon Tubing
33. 30 mL Vial (Screws up into Teflon Cover)
34. 200 mL Water Jacket (WJ2)
35. H₂O Out
FIG. 9 One configuration of AHT apparatus with:
36. UV Visible Spectrophotometer
37. to Flow Cell
38. FMI Metering Pump (P1)
39. Stir Plate
40. from Water Bath/Circulator
41. (TR) Titrant Reservoir
42. to WJ2
43. (P2) FMI Metering Pump
44. Viton Tubing
45. from TR
46. (WJ2) Water Jacket
47. to Water Bath/Circulator
48. Stir Plate
49. ChronTrol® Power Switch
50. Circuit A
51. Circuit B
52. Circuit C to Water Bath Power Supply
53. Integrator
FIG. 10—A schematic representation of one embodiment of a flow cell element
FIG. 11-R*eversible* Heithaus titration of SHRP core asphalt AAA-1-% Transmittance vs. Time with a Second 1.0 mL Addition of Toluene at approximately 1000 seconds and a First 1.0 mL Addition of Toluene at approximately 760 seconds.

Reaction containers may be configured as shown in FIGS. 3, 4 and 8 as follows. Teflon® reaction caps/reactor covers (adaptable to 25 mL reaction vials), and 25 mL test tube reaction vials may be used as the reaction containers or as reaction vials. The Teflon® reaction cap/reactor cover may be adaptable to 25 mL test tube reaction vials which are designed to fit inside a Kontes 200 mL water jacketed reaction beaker. The Teflon® reaction cap/reactor cover may hold a 25 mL test tube reaction vial, suspended within the beaker, further reducing the length of 1/32" ID-Teflon® tubing needed in the SCS. The unique round bottom design (e.g., "test tube" shape) of the 25 mL test tube reaction vials may be used to promote uniform, and undisturbed stiffing of the test solution during operation. A Teflon® reaction cap or lid, referred to more generally as a Teflon® lined solution containment element cap, may achieve a hermetic seal, effectively isolating the internal gaseous environment of the solution from the environment external of the solution containment element and the solution circulation system, for example. This hermetic seal is a type of gas exclusion element; excluding gas could also result from an apparatus or technique other than hermetic sealing. The term excluding gas from the solution does not necessarily mean all gases, as inert gases such as Argon, e.g. (or other gases other than oxygen) may exist in contact with the solution. The titration apparatus may comprise a solution containment hermetic seal such as a solution-titrant compatible tight fitting titration test container cap (or lid) which would exclude undesired gases such as oxygen from the solution containment element, and/or a titrant containment element hermetic seal, and/or a hermetically sealed titrant delivery element which would serve to isolate titrant and solution from the gaseous environment surrounding and external to their containment elements. The titration method, or more specifically the step of excluding gas from the solution, may comprise the step of pressurizedly purging substantially all oxygen from the solution containment element, as well as from other system components that might otherwise allow oxygen to contact the solution. This pressured purging may comprise the step of using an inert gas such as argon.

The entire procedure may proceed through a series of steps which lend themselves to both repeatability and practicality. As one aspect, sample preparation may include steps such as the following procedure.

1. Test samples may be prepared in 25 mL "test tube" vials (w/Teflon® lined seal 20/400-threaded caps).
2. Samples may be prepared in triplicate by transferring approximately 0.8 and 1.0 g of heavy residua or asphalt to two tared reaction vials and measuring sample masses to an accuracy of ±0.0005 g. All samples may be purged with Argon (Ar) gas and the vials may be sealed with Teflon® lined caps.
3. Prior to testing, the prepared samples may be dissolved in 2.000±0.001 mL of toluene (HPLC-grade). The reaction vials may be re-sealed with Teflon® lined caps and stored away from sunlight. One and one-half to two hours may be allowed for sample dissolution. A minimum of six hours is preferred for complete dissolution, and even a 24 hour period is strongly recommended.

Instrument Initialization may include steps such as the following procedure.

4. The spectrometer halogen lamp may be activated and allowed to warm up. Note that the tungsten Halogen lamp may require approximately 1 hour of warmup time.

5. The refrigerated bath/circulator may be activated. If a NesLab RTE-111-M refrigerated bath/circulator is used, a power switch is located on the left side panel of the "Micro" processor. As to this step, it may be noted that if the bath/circulator fails to power up, the circulator's microprocessor may need to be reset. The NesLab "Micro" processor may display "Prog" if not reset. This may occur if the Circulator alarms have been activated during previous usage. To reset the bath/circulator, simultaneously one may depress the "0" soft key on the bath/circulator "Micro" processor key pad while activating the main power switch. The NesLab "Micro" processor will read "OFF". To reactivate the bath/circulator, press the "On/Off" soft key on the "Micro" processor key pad. The "Micro" processor may now display a temperature reading in degree centigrade (° C.).

6. The remote sensor computer software up-link may then be set from the NesLab "Micro" processor keypad by depressing: "Sensor" then "Enter", then "RS232", and then "Enter". The NesLab bath/circulator should now be controlled from the computer.

7. The NesCom v 2.01 windows software may be activated by double clicking the NesCom icon and the following commands: Files, New, Controller and "Micro" processor bath and answering "yes" when prompted; "Is the Remote Sensor Enabled?" Note the micro processor bath icon may be displayed in "BLUE" when in standby mode.

8. Double clicking the "blue" micro processor bath icon, may permit one to confirm that the com address is set to "1", by selecting OK.

9. To initialize a working temperature program, one may open the following files from the main window; Program, Program Parameters . . . , and Open. Double clicking the file "ambientTemphold.prg", and selecting OK is the current command structure.

10. The "Micro" processor bath program may then be brought online by opening the following files from the main window: View, and Product Panel, and by answering "yes" when prompted; "Confirm that Unit is on". The temperature and setpoint values may now be displayed. Further, it may be noted that the "Micro" processor bath icon may display in GREEN when activated.

11. The operator may next minimize the NesCom and "Micro" processor Bath windows. The metering pumps calibration and the like may then proceed including steps such as the following procedure.

12. To calibrate the titrant pumps, the operator may mount a 1.000 mL syringe-graduated cylinder to a small lab stand using a test tube clamp or the like. Positioning the stand next to the titrant pump may assist.

13. The operator may then time the flow rate of each titrant pump with a stop watch, and each may be adjusted to a set value such as 0.300 mL/min or even 0.500 mL/min, the latter of which may also be a maximum.

14. To calibrate the circulation pumps, a 10.0 mL graduated cylinder may be mounted to a small lab stand using a test tube clamp. This may be positioned next to a titrant pump.

15. With a stop watch, the operator may time the flow rate of each circulation pump and adjust each flow rate to a value such as 8.0 mL/min, which may also be a minimum. The spectrometer portion of the system may then be set up through steps such as the following procedure.

16. If the currently preferred brand is used, the OceanOptics spectrometer(s) may be activated by loading the OOIBase32 software from Windows, and double clicking the OOIBase32 icon to load the program. The "Configure Hardware" window may then be displayed. The operator may change the "A/D Converter Type" to "ADC 1000/PC2000", and then select OK. The window; [Spectrum 1] may then be displayed.

17. The [Spectrum 1] window may be configured as the master spectrometer by default. Note, to activate additional spectrometers/windows, e.g., Slave 1 and Slave 2 spectrometers, select New from the File menu. Change the "Configure Hardware", i.e. change the "A/D Converter Type" to "ADC 1000/PC2000", and select OK. A second [Spectrum 2] window may be displayed for the Slave 1 spectrometer. To display the [Spectrum] windows simultaneously, select the Window menu then the Tile Vertically menu. Open the following files from theOOIBase32 main window; Spectrometer, and Open Configuration . . . , select the file "PC0A000.spec", then Open. The spectrometer address file may differ for each spectrometer bus A/D card present in the computer. See the manufacturer's specification for configuring any specific spectrometer address for a particular "AA0A000.spec" file. Either a PCS0A000.spec and/or IS0A000.spec file may correspond to the Slave 1 and Slave 2 spectrometers available with a particular instrument arrangement.

18. The operator may then set and calibrate each spectrometer for transmission mode operation as follows; in Scope Mode, the operator may adjust "Integ. Time (sec)" and the aperture such that at 740 nm the intensity is approximately 3500 units, i.e. with the aperture open, set "Integ. Time (sec)" to 14 to start. One may even set both the "Average" and "Boxcar" settings to 100 initially, then close the Halogen lamp shutter and select "Ctrl+D" (Dark spectrum). Open the Halogen lamp shutter and select "Ctrl+R" (reference spectrum). Select "Ctrl+Shift+T" or select the [T] icon to change the spectrometer detection mode to Transmission Mode. Repeat this procedure for all remaining open spectrum windows that will be operated. The data acquisition portion of the system may then be set up through steps such as the following procedure as illustrated using the OceanOptics Spectrometer.

19. A Time Acquisition Channel may be activated for a spectrum window, e.g., the OOIBase32 window; [Spectrum 1], previously opened. From the OOIBase32 main window, the operator may single click the header of the desired [Spectrum 1, 2, . . . ] window, and select Time Acquisition, then Configure, then Configure Time Channels. The Time Acquisition Channel Configuration window for Channel A, [Spectrum 1] window may now be displayed.

20. The operator may then enable the channel, by single clicking the blank boxes next to Enabled and Plotted, a check mark may be displayed in each box.

21. The "Spectrometer Channel" may then be set to Master if the [Spectrum 1] window has been selected as the (PC0A000.spec) spectrometer configuration. Note here that the "Spectrometer Channel" selection may change depending on the spectrometer configuration displayed, e.g., to enable the Slave 1 channel, select the [Spectrum 2] window by single clicking the header of the window and select Time Acquisition, then Configure, then Configure Time Channels, set the "Spectrometer Channel" to Slave 1 for the PCS0A000.spec file associated with the window.

22. The operator may then set the detection wavelength by clicking inside the box next to "Wavelength (nm)" and typing in 740 to set the detection wavelength to 740 nm. Here note that the three remaining parameters may be pre-set values and may remain as; Factor (multiply)=1, Bandwidth (pixels)=0, and Offset (add)=0. Select OK to confirm the settings and exit.

23. The operator may then set the software to stream data to files for Master and Slave channels, from the Time Acquisition menu, by selecting Configure, then Configure Acquisition . . . , and checking the Stream Data to Disk and Show Values in Status Bar boxes. Note that it may be necessary to disable Save Full Spectrum with Each Acquisition, Save Every Acquisition, or Continue Until Manually Stopped if they are selected.

24. The time file settings may be set by selecting the Time Acquisition menu, and selecting: "Write Data to Disk Every"=1 acquisition, "Initial Delay"=0, "Frequency"=100 milliseconds, and "Duration"=8 Hour.

25. To save the "percent Transmission" versus "time" data to the Windows Desktop, the operator may need to select the "Stream and Autosave Filename" box and change it to: C:\Desktop\timetestMASTER.Time. Select OK to accept the file name settings and exit. This file name may represent the file of the first of two solutions that will be titrated for a given asphalt in a sample set. Normally the C:\Desktop\timetestMASTER.Time file may correspond to the more dilute solution in the sample set. A second streamed data file may be saved as "C:\Desktop\timetestSLAVE.Time", such as corresponding to the more concentrated solution data file in the sample set.

26. The operator may then activate the time channel window "ready for testing" by opening Time Acquisition and selecting the Activate Time Acquisition option from the active window, [Spectrum 1, 2, . . . ]. Here, note that the time acquisition icon tool button may be used to activate the Time Acquisition menu as an alternative. The titration and circulation pumps may then be calibrated through steps such as the following procedure.

27. Prior to sample testing, the circulation pumps (CP) and titrant delivery pumps (TDP) may be adjusted to predetermined flow rates.

28. The operator may set each CP-flow rate by placing the intake tube in a vial of toluene and the output tube in a 10.0 mL graduated cylinder. The flow rate may then be timed with a stop watch and the CP-flow rate may be adjusted to 8.0 mL/min, which may also be a minimum, each perhaps reported to an accuracy of ±0.1 mL/min.

29. The TDP-flow rates may similarly be timed and adjusted to 0.300 (or 0.500 which may also be a maximum) and report to an accuracy ±0.001 mL/min. The spectrometer may then be re-zeroed through steps such as the following procedure.

30. The operator may fill a 50 mL beaker half-full with HPLC-grade toluene and may pump the toluene through the circulation pump/flowcell system into a second 50 mL beaker. Likely it may be desirable to discard the first few milliliters of solvent and replace the beaker, and continue the process until the disposed solvent is clear.

31. The operator should then verify that the spectrometer is in % T-mode, obtain a Dark and a Reference spectrum for the active spectrometer. The operator closes the Halogen lamp shutter and select "Ctrl+D". Then, the operator may open the Halogen lamp shutter and select "Ctrl+R". This step may be repeated prior to each sample tested.

32. The operator may then adjust the spectrum % T scale by selecting View, then Spectrum Scale, then Set Scale. When the Scale adjustment window appears, set the "X-Axis (nm) Minimum" value may be set to 739.99, and set the "X-Axis (nm) Maximum" value may be set to 740.1. A titration procedure may then be performed through steps such as the following procedure.

33. The operator may place a stir bar into a 25 mL "test tube" vial containing the 0.400 g/mL sample. The Teflon® cap/Reactor cover may then be screwed onto the vial. The operator may then set the vial/reactor cover into the water filled 200 mL jacketed reaction beaker and engage the stir bar. The stir plate may be set to speed "4". Operation may then proceed to allow sufficient time (3-5 minutes) for the sample to come to temperature equilibrium.

34. The CP-tubing ends may be inserted through the holes available in the top of the Teflon® cap/Reactor cover. Here the operator may adjust the CP-tubing ends either up or down to prevent them from hindering the stir bar.

35. The titrant pump dispenser-tube end may then be inserted through an available hole in the Teflon® cap/reactor cover.

36. The operator may then initiate the titration experiment by simultaneously engaging the titrant pump, activated from the power strip (Switch #1), and the time acquisition play icon, activated from within the [Spectrum] window with the mouse. Here, note that when the time acquisition play icon is activated, the time acquisition pause icon and the time acquisition stop icon may also become activated. These icons may be used to pause, or stop the stream of data to the time acquisition data file during a test.

37. The operator may then monitor the status of the titration on the status bar located at the bottom of the [Spectrum] window. A time plot may also be displayed on the spectrum for monitoring. The spectrum Transmission intensity (redline) may increase over time, then decrease. As this value increases then decreases, the spectrum line will likely be observed to rise then fall, this signifies that the flocculation onset endpoint has been reached. The operator may then allow a few seconds of time to pass to confirm the flocculation onset point and then act to deactivate the titrant pump (Power Strip Switch #1), and the data streaming (time acquisition stop icon). Note that each spectrum window time acquisition play icon and titrant pump On/Off switch may be set to be activated and deactivated independently of other time acquisition play icons and titrant pump On/Off switches.

38. When the test is complete, the operator may remove the circulation pump intake tube end from the sample, and pump the residual sample solution back into the reaction vial. It may then be desirable to remove the second tube end and pump several milliliters of toluene through the system using 50 mL beakers.

39. The tested sample may then be removed, the vial rinsed, and aired in the hood. The Teflon® reactor cover may then be cleaned and dried with a cold-trap vacuum line.

40. The above steps may also be repeated to titrate additional samples. In repeating steps, it may be helpful to note that tests may be performed by titrating a sample at two concentrations, e.g., 0.400-g/mL and 0.500 g/mL. It may be desirable to save the 0.400-g/mL sample run as C:\Desktop\timetestMASTER.Time and the 0.500-g/mL sample run as C:\Desktop\timetestSLAVE.Time.

In the above testing, sample runs may be performed by loading vials (30 mL) of sample into the second water jacket (WJ2), generally from least to most concentrated in solution, by carefully placing a small stir bar into a vial of the solution and screwing the vial into the Teflon® cover. The vial/cover may be placed into the second water jacket (WJ2). The two ends of the Viton® tubing, which run from the circulating pump (P1) and from the flow cell, respectively, may be placed through holes in the cover down into the solution. As the asphalt solution circulates through the flow cell, the percent transmittance reading of the spectrophotometer may decrease, then stabilize at some minimum value of percent transmittance, corresponding to the percent of light transmitted through a solution of asphalt in toluene with no titrant added. One end of the Viton® tubing running from the titrant pump (P2) may be placed down into the vial well above the surface of the asphalt solution. A probe thermometer (not shown) may also be placed down into the test solution and used to monitor the temperature of the solution as the titration proceeds. To begin the titration, the titrant pump (P2) and the integrator may be started at the same time.

Further, in establishing the titrant flow, a maximum titrant (2,2,4-trimethylpentane-iso-octane and methyl ethyl ketone-MEK) flow rate may be important. In one embodiment, a maximum titrant addition rate not to exceed 0.5 mL/min has been determined to work as the most efficient flow rate for the current instrument configuration. Furthermore, higher viscosity titrants, such as 2-ethyl-1-hexanol (iso-octanol) may be used in place of 2,2,4-trimethylpentane (iso-octane) or methyl ethyl ketone (MEK). In such use, the maximum titrant addition rate may be selected so as to not exceed 0.2 mL/min to produce repeatable test results. Adding a titrant at maximum rate, or more generally adding a titrant at an optimal solubility reduction response rate, may be important for efficient and accurate operation of the titration apparatus. While of course, such rates may be varied, these maximum titrant addition rates have been determined based on a number of samples tested. Regardless of the rate used, it may be noted that the reagent grades may also be important to the procedure. For example, all of the reagents; 2,2,4-trimethylpentane (iso-octane), toluene, 2-ethyl-1-hexanol (iso-octanol), methyl ethyl ketone (MEK), and the like used in this procedure may be at a minimum of HPLC grade.

Figure 5:
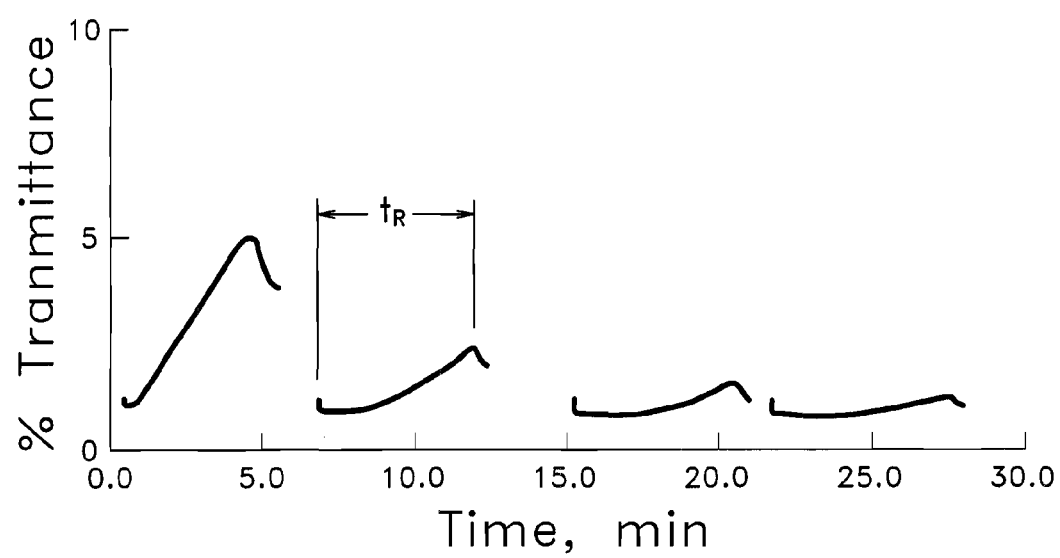
FIG. 5 shows representative transmission vs time results for various samples: Percent transmittance versus titrant delivery time (flocculation curves) plotted for AAD-1 SHRP core asphalt solutions prepared at four different concentrations, titrated with iso-octane (titrant flow rate $v_T$=0.350=0.005 mL/min) with:
$t_R$: Retention Time to Peak Apex
υT: Titrant Flow Rate
$V_T=t_R \times v_T$: Volume of Titrant at Flocculation Onset FIG. 6
Figure 6:
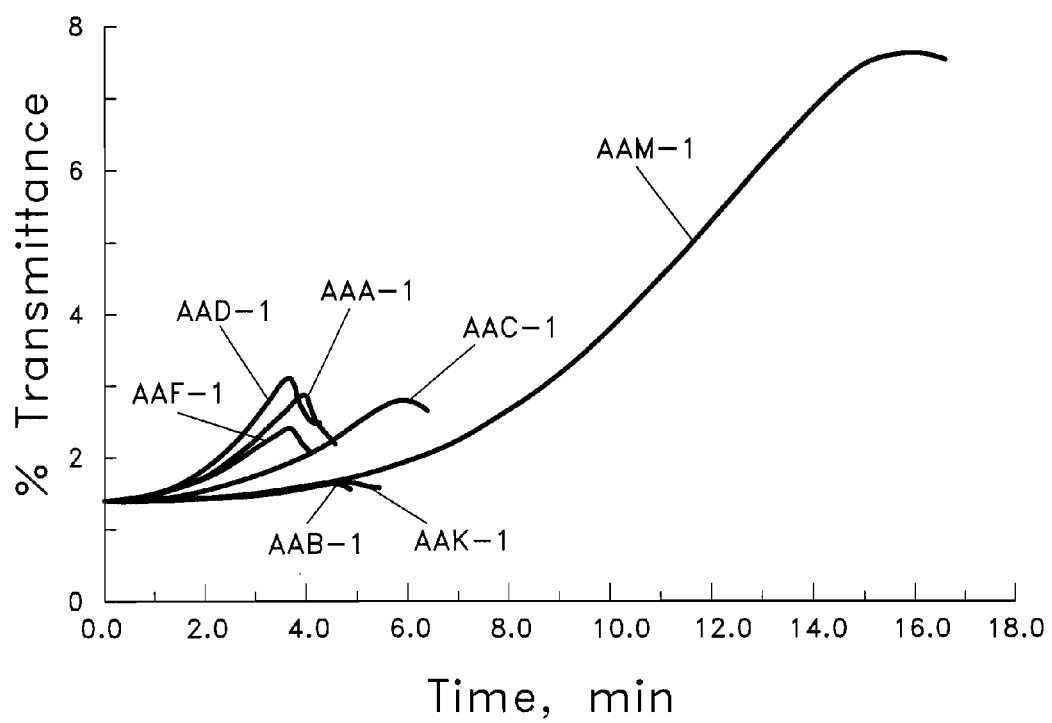
FIG. 6 shows a percent transmittance versus titrant delivery time (flocculation curves) plotted for 7 SHRP core asphalt solutions prepared as 1.0000=0.0005 g of asphalt dissolved in 1.000=0.005 mL of toluene,
titrated with iso-octane (titrant flow rate 1)$_T$=0.350=0.005 mL/min)
Figure 7:
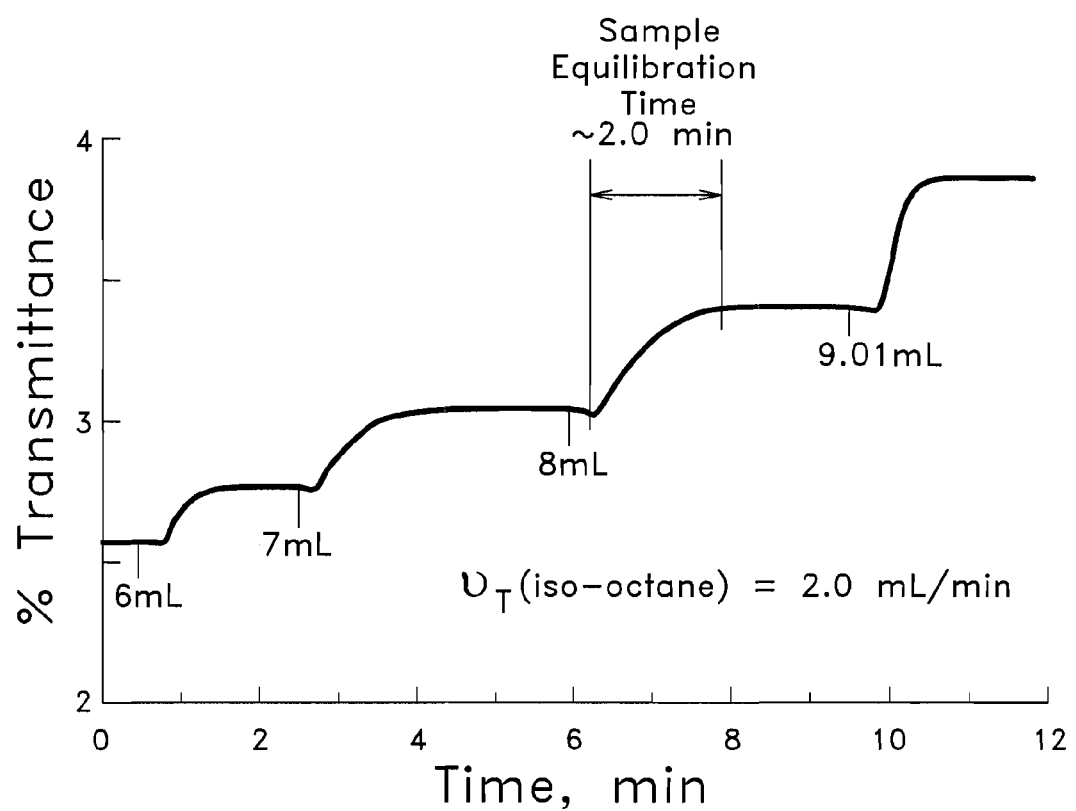
FIG. 7 Percent transmittance versus time plotted on a strip chart recorder for a solution of SHRP core asphalt
(AAM-1) dissolved in toluene, continuously circulated through a UV-visible spectrophotometric detection
system as 1.0 mL aliquots of iso-octane are added intermittently.
Figure 12:
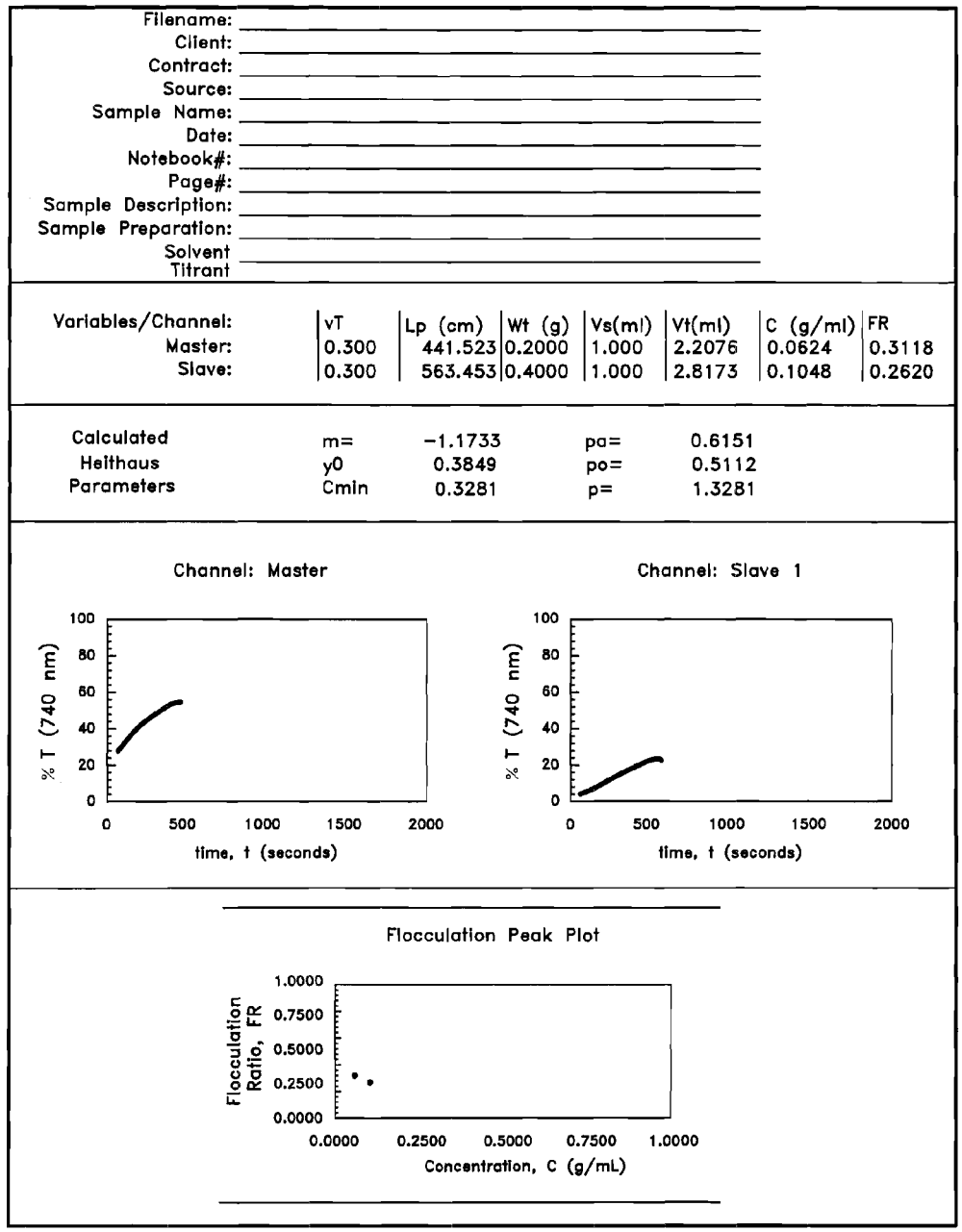
FIG. 12-S*ample* Graph of an Analyzed Spectrophotometer reading

As mentioned above, as the titration proceeds a flocculation peak will likely develop. A representative example of such is shown in FIGS. 5, 6 and even FIG. 7. As may be understood, the initial increase in percent transmittance (% T) of the flocculation peak, plotted as a function time in which titrant is added at a constant flow rate, is due to the dilution of the test solution as iso-octane is added. During this time period, dispersed phase molecular associations likely remain in solution. A maximum % T value is then reached. At this point, the integrator may print out a retention time. The % T value versus time plot, such as that shown in the FIGS. 5, 6, 7 and 12 then may decrease due to the scattering of light as dispersed phase molecular associations begin to precipitate from the test solution. The flocculation onset point is then taken as the retention time value recorded at maximum % T. At the flocculation onset point the temperature of the solution may then be recorded. FIGS. 5 and 6 show a plot of percent transmittance versus time for a flow rate of $\upsilon_T$ (mL/min) for four samples of SHRP core asphalt AAD_1 dissolved in toluene at four different concentrations. While, of course, displays may be varied, one type of display that may be provided by the analysis software is shown in FIG. 12.

Figure 11:
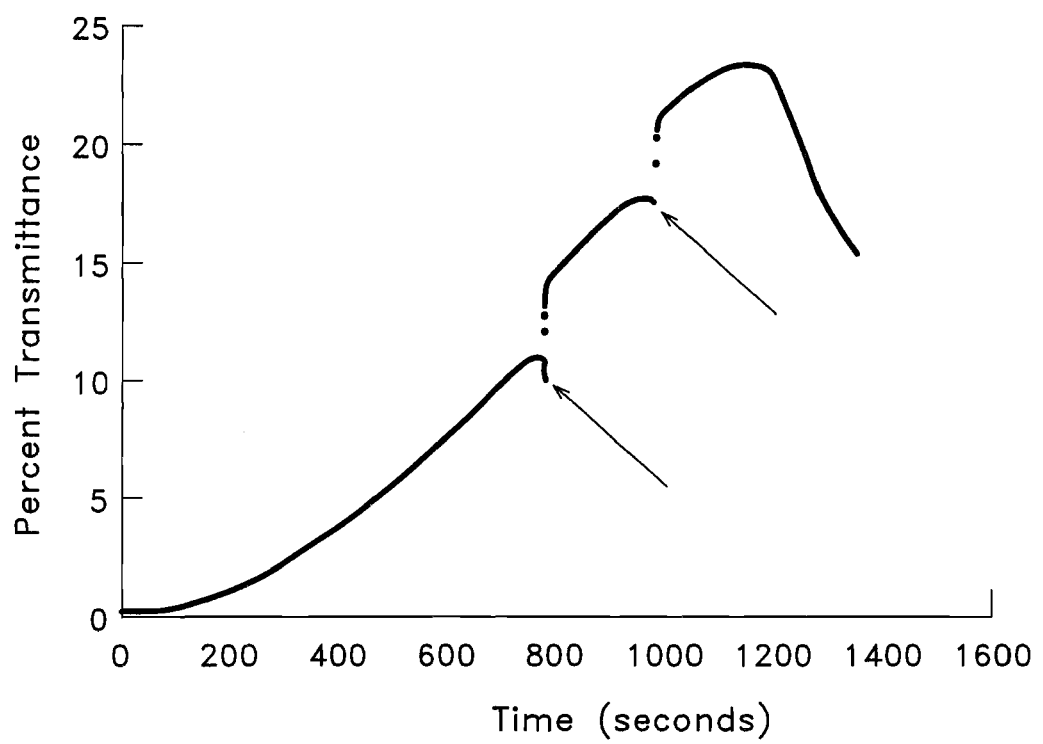

In addition, the reversible Heithaus titration procedure may be used to measure Heithaus parameters $p_a$, $p_o$ and P on single samples based on a "back" titration technique. This variation may be performed by first preparing a 1.0 g sample of asphalt dissolved in 2.0 mL of toluene in 30 mL vials, then titrating the solution with iso-octane (2,2,4-triethylpentane at a constant flow rate in accord with the above procedure. As the titration proceeds, each onset of flocculation may be closely monitored by monitoring a solution change index, or more generally a parameter, such as turbidity, of the solution. When the first flocculation onset caused by the addition of the titrant is observed (or more generally, upon achieving a threshold solution change), signified by, for example, a change in direction of the percent transmittance versus time plot, the step of adding a solvent to the solution, such as quickly adding a 1.0 mL aliquot of toluene (for example) may be performed. More generally, upon achieving a threshold solution change, the step of altering a character of the solution to eliminate (where eliminate also means substantially eliminate) the first threshold solution change may be performed. This addition of toluene, e.g., or other solvent to the sample solution as the titration continues uninterrupted tends to mostly re-dissolve the sample, effectively achieving a higher solubility parameter for the solution and by diluting the sample to accommodate a second, and possibly a third measurement of the flocculation onset in-situ. After flocculation is observed, the step of preliminarily assessing a parameter (such as a Heithaus parameter(s) and/or compatibility and/or added titrant amount since any prior flocculation that may have existed, and/or time since any prior flocculation (or since the initiation of titrant addition)) may be performed. Indeed, the experiment may repetitively achieve additional threshold solution changes, which may each be detected by a repetitive solution threshold change detector that may comprise, for example, an integrator and/or a computer program, among other components. As in any titration method, the temperature of the solution may be controlled by a temperature control element such as a circulating water bath. FIG. 11 shows a plot of percent transmittance versus time (at constant titrant flow rate) for such a reversible Heithaus titration experiment of SHRP core asphalt AAA-1.

The above procedure may be fully automated if a programmable pump or solvent dispenser is used to deliver the "back titrant" toluene to the sample solution as indicated by differential integration of the flocculation onset point, as the titration proceeds. More generally, any determination of the maximum % transmittance value may suffice. Upon such determination, an automatic solvent introduction system, or more generally a solvent introduction system may be activated. A solution character alteration element, such as a metered solvent addition system (which may comprise a pump), may be responsive to a solution threshold change detector via, e.g., an integrator and/or computer that monitors a parameter such as % transmittance v. time of titrant addition (the integrator and/or computer may signal the maximum of this graph). Addition of may be performed in a metered fashion by, e.g., a metered toluene addition element or a metered benzene addition element.

As one example, Table 1 lists some experimental values, averages and standard deviations in measured values of $p_a$, $p_o$ and P for eight SHRP core and six non-core asphalts using the reversible Heithaus titration technique.

Finally, at the completion of a run, the Viton® tubing running from the circulating system may be drawn up out of solution and the remaining solution in the circulating system may be pumped out into the sample vial. The tubing may then be placed into a vial containing toluene. Clear toluene may be circulated through the pump (P1), tubing, and the flow cell clearing the system. The Viton® tubing running from the titrant pump (P2) may then be placed into the top of a graduated cylinder and the flow rate of the titrant may be timed with a stop watch. A second sample may then be loaded into the system and the procedure repeated. When testing is completed, all glassware used during the procedure may be rinsed with wash toluene and allowed to dry in a vented hood. The circulation pump may be flushed with fresh LC-grade toluene, and then pumped dry of solvent, and all components of the system may be shut down.

As mentioned, the Heithaus parameters can be determined from the above procedures. data calculation may involve the following variables:

Sample weights, $W_a$ (g)
Volume of solvent (toluene), $V_S$ (mL)
Detection wavelength, $\lambda_D$ (nm)
Titrant flow rate, $\upsilon_T$ (mL/min)
Retention time at peak apex (flocculation onset), $t_R$ (min)
Solution temperature at flocculation onset, $T_{soln}$ (° C.)

The volume of titrant ($V_T$, mL) added to each sample to initiate flocculation may be calculated as the product of the time (reported as the peak retention time $t_R$, min) required to deliver titrant at a flow rate of $\upsilon_T$ (mL/min) to the test solution. $V_T$ (mL) may be calculated as follows:

$$V_T = t_R \upsilon_T \quad (1\_1)$$

Values of $V_T$, $V_S$, and $W_a$ may be used to calculate flocculation ratios and dilution ratio concentrations, FR and C, for each run (which may consist of a set of test solutions of different concentrations of a given asphalt) using the following relationships:

$$FR = V_S/(V_S + V_T). \quad (1\_2)$$

and $$C = W_a/(V_S + V_T) \quad (1\_3)$$

A linear analysis may be used to derive the equation for the line FR=aC+b using values of $FR_i$ plotted versus values of $C_i$. Heithaus parameters may then be calculated by extrapolating the line to the x and y axis, where the x and y intercepts are formally referred to as the dilution ratio minimum ($C_{min}$) and the flocculation ratio maximum ($FR_{max}$), respectively:

$$b = FR_{max} @ C = 0 \quad (1\_4)$$

and $$-a/b = C_{min}^{-1} @ FR = 0 \quad (1\_5)$$

Using values of $FR_{max}$ and $C_{min}$, Heithaus parameters $p_a$, $p_o$, and P may be calculated as follows:

$$P_a = 1 - FR_{max} \quad (1\text{-}6)$$

$$p_o = FR_{max}[(1/C_{min}) + 1] \quad (1\_7)$$

$$p = p_o/(1 - p_a) \quad (1\_8)$$

As part of a representative automated routine, the Heithaus parameters may be calculated using a Excel macro, named AFTCalc.xls. To open this, an operator need only "double click" the AFTCalc.xls file from the list of desktop files, and "Click" the Enable Macro option when prompted. Next the operator could select the Tools pull down menu, then select Macro, then Macro . . . , (Alt+F8), and finally Run. The macro may open a template file, such as a AFT Template with graphs.xls and the previously saved time files; C:\Desktop\timetestMaster.Time and CADesktop\timetestSLAVE.Time. When the macro has completed the calculation of Heithaus parameters, the operator may need only save the file with an appropriate name.

It is important to understand a few of the more practical improvements in production technique and asphalt processing that are enabled by this accurate Heithaus parameter determination method. It is now possible to accurately predict the compatibility of an asphaltic composite, more commonly known as an asphalt blend, and thus to more efficiently and cost-effectively prepare a compatible asphalt composite in commercial quantities. An asphalt producer such as a refiner may obtain a quantity of a first type of asphalt and a quantity of a second type of asphalt, which may be of lesser quality or lesser cost per ton than the first quantity of asphalt. Perhaps also there may exist a third type. The asphalts may merely be of different stocks. Essentially, the producer may use the automated Heithaus parameter determination method to affirmatively and accurately an optimal asphalt mix ratio to achieve a desired result such as cost savings. A producer may wish to mix two or more different types of asphalt (for example, asphalt from different stocks) in optimal mix ratio such that the resulting composite is still compatible. It may be that the producer has a first superior character asphalt substance and a second inferior asphalt substance. In order to do this, the producer (or more generally a tester) may create a first asphalt composite by mixing in a predetermined ratio two or more types of asphalt to create a first intermediate asphaltic composite. The tester may then use the automated Heithaus parameter titration apparatus and method described herein to accurately determine a first set of Heithaus parameters, which may then be used to accurately generate a first compatibility measurement of the first intermediate composite blend (also known as accurately determine the long term compatibility). The tester may then also create an additional intermediate asphaltic composite with predetermined ratio(s) that is(are) different from the first asphaltic composite. The tester may then use the automated Heithaus parameter titration apparatus and method described herein to accurately determine an additional set of Heithaus parameters corresponding to each of the additional intermediate asphalt composites as may have been created. The next steps would involve comparing a plurality of compatibility measurements of the intermediate asphaltic composites and then selecting an optimal asphalt mix ratio based upon this plurality of compatibility measurements. Upon such selection, the asphalt producer would then mix a tonnage amount of the different types of the asphalts in order to arrive at an optimal compatible composite. Relatedly, a titration apparatus used in order to determine the suitability (by measuring, e.g., compatability) of a composite asphalt may be said to comprise a composite asphalt containment element; a titration apparatus used in this capacity is said to be an optimal mix ratio determination system. To improve efficiency, such an apparatus may comprise multiple composite asphalt containment elements, as well as multiple solution character determination elements, such as spectrophotometers and/or computers that may be used to automatically determine Heithaus parameters. Any component that serves to aid in the determination of Heithaus parameters, such as, but not limited to, a spectrophotometer and/or a computer and/or an integrator may be used multiply as a multiple Heithaus parameter determination element.

Another related production technique enabled by the present invention's accurate Heithaus parameter determination has to do with replacing a certain type of asphalt that perhaps is ordered by a customer that the producer does not have in sufficient quantity to meet the customer's demands. Essentially, upon accepting a required specification range set by a customer's intended use, a replacement asphaltic substance may be used to meet the customer's demands upon use of the present invention's accurate Heithaus parameter determination capability. A mix ratio may be determined according to the customer's order and the amounts of different types of asphalt available. This mix ratio may then be used to create a sample for which an accurate Heithaus parameter determination, and thus an accurate compatibility measurement is possible.

As can be easily understood from the foregoing, the basic concepts of the present invention may be embodied in a variety of ways. It involves both analysis techniques as well as devices to accomplish the appropriate analysis. In this application, the analysis techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims herein included.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied for support of the claims of this application. It should be understood that any such language changes and broad claiming is herein accomplished. This full patent application is designed to support a patent covering numerous aspects of the invention both independently and as an overall system.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "pump" should be understood to encompass disclosure of the act of "pumping"—whether explicitly discussed or not—and, conversely, were there effectively disclosure of the act of "pumping", such a disclosure should be understood to encompass disclosure of a "pump" and even a "means for pumping." Such changes and alternative terms are to be understood to be explicitly included in the description.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference.

Finally, all references listed in the list of References To Be Incorporated By Reference In Accordance With The patent Application or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to claim at least: i) each of the analysis devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed, xi) processes performed with the aid of or on a computer as described throughout the above discussion, xii) a programmable apparatus as described throughout the above discussion, xiii) a computer readable memory encoded with data to direct a computer comprising means or elements which function as described throughout the above discussion, xiv) a computer configured as herein disclosed and described, xv) individual or combined subroutines and programs as herein disclosed and described, xvi) the related methods disclosed and described, xvii) similar, equivalent, and even implicit variations of each of these systems and methods, xviii) those alternative designs which accomplish each of the functions shown as are disclosed and described, xix) those alternative designs and methods which accomplish each of the functions shown as are implicit to accomplish that which is disclosed and described, xx) each feature, component, and step shown as separate and independent inventions, xxi) the various combinations and permutations of each of the above, and xxii) each potentially dependent claim or concept as a dependency on each and every one of the independent claims or concepts presented. In this regard it should be understood that for practical reasons and so as to avoid adding potentially hundreds of claims, the applicant may eventually present claims with initial dependencies only. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

The claims set forth in this specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. An automated flocculation titration method for accurate determination of Heithaus parameters and/or prediction of compatibility of blended asphalt comprising the steps of:
   a. creating a solution by dissolving a first blended asphalt in a solvent; and
   b. controllably adding a titrant to said solution for a first time to cause a first flocculation onset, while monitoring light transmittance through said solution;
   c. determining a first added titrant amount corresponding to a first maximum transmittance for said solution, said first maximum transmittance defining said first flocculation onset;
   d. adding said solvent to said solution so as to eliminate said first flocculation onset;
   e. controllably adding said titrant to said solution for a second time to cause a second flocculation onset, while monitoring light transmittance through said solution; and
   f. determining a second added titrant amount corresponding to a second maximum transmittance for said solution, said second maximum transmittance defining said second flocculation onset; and
   g. determining accurate Heithaus parameters and/or a compatibility estimate for said first blended asphalt.

2. An automated flocculation titration method for accurate determination of Heithaus parameters and/or prediction of compatibility of blended asphalt as described in claim 1 further comprising the step of repeating said steps (a) through (g) for each of at least one additional blended asphalt.

3. An automated flocculation titration method for accurate determination of Heithaus parameters and/or prediction of compatibility of blended asphalt as described in claim 2 further comprising the step of comparing a plurality of Heithaus parameters and/or compatibility estimates for said blended asphalts.

4. An automated flocculation titration method for accurate determination of Heithaus parameters and/or prediction of compatibility of blended asphalt as described in claim 3 further comprising the step of selecting an optimal asphalt mix ratio based upon said step of comparing.

5. The automated flocculation titration method for accurate determination of Heithaus parameters and/or prediction of compatibility of blended asphalt described in claim 1 and further comprising the step of determining a third added titrant amount corresponding to a third maximum transmittance for said solution.

6. The automated flocculation titration method for accurate determination of Heithaus parameters and/or prediction of compatibility of blended asphalt described in claim 1 and further comprising the step of maintaining said solution at a desired temperature throughout said method.

7. The automated flocculation titration method for accurate determination of Heithaus parameters and/or prediction of compatibility of blended asphalt described in claim 1 and further comprising the step of excluding gas from said solution.

8. The automated flocculation titration method for accurate determination of Heithaus parameters and/or prediction of compatibility of blended asphalt described in claim 1 wherein said step of controllably adding a titrant to said solution for a first time comprises the step of continuously adding said titrant to said solution and wherein said step of controllably adding a titrant to said solution for second time comprises the step of continuously adding said titrant to said solution.

9. The automated flocculation titration method for accurate determination of Heithaus parameters and/or prediction of compatibility of blended asphalt described in claim 1 wherein said step of controllably adding a titrant to said solution for a first time comprises the step of controllably adding a titrant selected from the group consisting of: aliphatic hydrocarbon substances and alcohol substances.

10. The automated flocculation titration method for accurate determination of Heithaus parameters and/or prediction of compatibility of blended asphalt described in claim 1 wherein said step of creating a first solution by dissolving at said blended asphalt in a solvent comprises the step of mixing said blended asphalt with a solvent selected from the group consisting of: toluene and benzene.

11. The automated flocculation titration method for accurate determination of Heithaus parameters and/or prediction of compatibility of blended asphalt described in claim 1 wherein said step of controllably adding a titrant to said solution for a first time comprises the step of controllably adding iso-octane.

12. The automated flocculation titration method for accurate determination of Heithaus parameters and/or prediction of compatibility of blended asphalt described in claim 1 wherein said step of controllably adding a titrant to said solution for a first time to cause flocculation, while monitoring transmittance of said solution comprises the step of controllably adding a titrant to said solution for a first time while monitoring visible light transmittance of said solution.

13. The automated flocculation titration method for accurate determination of Heithaus parameters and/or prediction of compatibility of blended asphalt described in claim 1 wherein said blended asphalt comprises asphalt.

* * * * *